United States Patent
Michelson

(10) Patent No.: US 7,399,301 B2
(45) Date of Patent: *Jul. 15, 2008

(54) INSTRUMENTATION FOR USE WITH DYNAMIC SINGLE-LOCK ANTERIOR CERVICAL PLATE SYSTEM HAVING NON-DETACHABLY FASTENED AND MOVEABLE SEGMENTS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 834 days.

This patent is subject to a terminal disclaimer.

(21) Appl. No.: 10/809,242

(22) Filed: Mar. 25, 2004

(65) Prior Publication Data

US 2004/0181229 A1    Sep. 16, 2004

Related U.S. Application Data

(62) Division of application No. 10/160,086, filed on Jun. 4, 2002, now Pat. No. 7,097,645.

(60) Provisional application No. 60/296,059, filed on Jun. 4, 2001, provisional application No. 60/356,318, filed on Feb. 12, 2002.

(51) Int. Cl.
    *A61B 17/56* (2006.01)
    *A61B 17/58* (2006.01)
(52) U.S. Cl. .................... 606/71; 606/69; 606/70
(58) Field of Classification Search ............ 606/60, 606/61, 69, 70, 71
    See application file for complete search history.

(56) References Cited

U.S. PATENT DOCUMENTS

| 1,105,105 A | 7/1914 | Sherman |
| 3,604,414 A | 9/1971 | Borges |
| 3,659,595 A | 5/1972 | Haboush |
| 3,900,025 A | 8/1975 | Barnes, Jr. |
| 4,034,418 A | 7/1977 | Jackson et al. |
| 4,289,123 A | 9/1981 | Dunn |
| RE31,628 E  | 7/1984 | Allgower et al. |

(Continued)

FOREIGN PATENT DOCUMENTS

DE    4007306    5/1991

(Continued)

OTHER PUBLICATIONS

AESCULAP Scientific Information Booklet; *Anterior Cervical Fusion and Interbody Stabilization with the Trapezial Osteosynthetic Plate Technique* by Wolfhard Casper; Feb. 1986.

(Continued)

*Primary Examiner*—Pedro Philogene
(74) *Attorney, Agent, or Firm*—Martin & Ferraro, LLP

(57) ABSTRACT

An anterior cervical plating system having moveable plate segments to vary the overall length of the plate, moveable to allow and/or cause intersegmental compression of vertebral bodies, and coupled together by a non-detachable fastener. The plating system includes locking elements for locking only one bone screw to the plate, instrumentation, and method for installation thereof. The plating system is capable of both passive and active dynamization and the ability to produce the former from the latter.

63 Claims, 25 Drawing Sheets

U.S. PATENT DOCUMENTS

| | | |
|---|---|---|
| 4,467,809 A | 8/1984 | Brighton |
| 4,488,543 A | 12/1984 | Tornier |
| 4,493,317 A | 1/1985 | Klaue |
| 4,503,848 A | 3/1985 | Caspar et al. |
| 4,599,086 A | 7/1986 | Doty |
| 4,651,724 A | 3/1987 | Berentey et al. |
| 4,743,256 A | 5/1988 | Brantigan |
| 4,794,918 A | 1/1989 | Wolter |
| 4,795,804 A | 1/1989 | Urist |
| 4,936,848 A | 6/1990 | Bagby |
| 5,034,418 A | 7/1991 | Yamagishi et al. |
| 5,041,113 A | 8/1991 | Biedermann et al. |
| 5,053,036 A | 10/1991 | Perren et al. |
| 5,127,912 A | 7/1992 | Ray et al. |
| 5,129,903 A | 7/1992 | Luhr et al. |
| 5,147,361 A | 9/1992 | Ojima et al. |
| 5,167,665 A | 12/1992 | McKinney |
| 5,180,381 A | 1/1993 | Aust et al. |
| 5,190,544 A | 3/1993 | Chapman et al. |
| 5,209,751 A | 5/1993 | Farris et al. |
| 5,234,431 A | 8/1993 | Keller |
| 5,300,073 A | 4/1994 | Ray et al. |
| 5,330,477 A | 7/1994 | Crook |
| 5,344,421 A | 9/1994 | Crook |
| 5,364,399 A | 11/1994 | Lowery et al. |
| 5,397,363 A | 3/1995 | Gelbard |
| 5,423,826 A | 6/1995 | Coates et al. |
| 5,470,333 A | 11/1995 | Ray |
| 5,520,690 A | 5/1996 | Errico et al. |
| 5,531,746 A | 7/1996 | Errico et al. |
| 5,531,747 A | 7/1996 | Ray |
| 5,549,612 A | 8/1996 | Yapp et al. |
| 5,558,674 A | 9/1996 | Heggeness et al. |
| 5,569,250 A | 10/1996 | Sarver et al. |
| 5,578,034 A | 11/1996 | Estes |
| 5,593,409 A | 1/1997 | Michelson |
| 5,601,553 A | 2/1997 | Trebing et al. |
| 5,605,938 A | 2/1997 | Roufa et al. |
| 5,607,426 A | 3/1997 | Ralph et al. |
| 5,616,142 A | 4/1997 | Yuan et al. |
| 5,628,781 A | 5/1997 | Williams et al. |
| 5,643,265 A | 7/1997 | Errico et al. |
| 5,646,142 A | 7/1997 | Dantanarayana et al. |
| 5,662,652 A | 9/1997 | Schafer et al. |
| 5,672,177 A | 9/1997 | Seldin |
| 5,676,666 A | 10/1997 | Oxland et al. |
| 5,676,703 A | 10/1997 | Gelbard |
| 5,681,313 A * | 10/1997 | Diez .................... 606/69 |
| 5,713,900 A | 2/1998 | Benzel et al. |
| 5,722,977 A | 3/1998 | Wilhelmy |
| 5,728,127 A | 3/1998 | Asher et al. |
| 5,735,853 A | 4/1998 | Olerud |
| 5,735,899 A | 4/1998 | Schwartz et al. |
| 5,741,258 A | 4/1998 | Klaue et al. |
| 5,755,796 A | 5/1998 | Ibo et al. |
| 5,766,254 A | 6/1998 | Gelbard |
| 5,800,433 A | 9/1998 | Benzel et al. |
| D402,032 S | 12/1998 | Stone |
| 5,843,082 A | 12/1998 | Yuan et al. |
| 5,865,848 A | 2/1999 | Baker |
| 5,866,113 A | 2/1999 | Hendriks et al. |
| D406,646 S | 3/1999 | Stone |
| 5,876,402 A | 3/1999 | Errico et al. |
| 5,899,939 A | 5/1999 | Boyce et al. |
| 5,902,304 A | 5/1999 | Walker et al. |
| 5,904,683 A | 5/1999 | Pohndorf et al. |
| 5,947,893 A | 9/1999 | Agrawal et al. |
| 5,951,558 A | 9/1999 | Fiz |
| 5,954,722 A | 9/1999 | Bono |
| 5,954,725 A | 9/1999 | Sherman et al. |
| 5,964,760 A | 10/1999 | Richelsoph |
| 5,964,762 A | 10/1999 | Biedermann et al. |
| 5,964,763 A | 10/1999 | Incavo et al. |
| 5,968,098 A | 10/1999 | Winslow |
| 6,022,350 A | 2/2000 | Ganem |
| 6,030,389 A | 2/2000 | Wagner et al. |
| 6,045,554 A | 4/2000 | Grooms et al. |
| 6,087,555 A | 7/2000 | Duntan et al. |
| 6,106,527 A | 8/2000 | Wu et al. |
| 6,106,557 A | 8/2000 | Robioneck et al. |
| 6,117,135 A | 9/2000 | Schlapfer |
| 6,136,001 A | 10/2000 | Michelson |
| 6,139,316 A | 10/2000 | Sachdeva et al. |
| 6,139,550 A | 10/2000 | Michelson |
| 6,152,927 A | 11/2000 | Farris et al. |
| 6,159,213 A | 12/2000 | Rogozinski |
| 6,193,721 B1 | 2/2001 | Michelson |
| D440,311 S | 4/2001 | Michelson |
| 6,217,580 B1 | 4/2001 | Levin |
| 6,224,602 B1 | 5/2001 | Hayes |
| 6,224,607 B1 | 5/2001 | Michelson |
| 6,228,085 B1 | 5/2001 | Theken et al. |
| 6,235,034 B1 | 5/2001 | Bray |
| 6,235,059 B1 | 5/2001 | Benezech et al. |
| 6,258,089 B1 | 7/2001 | Campbell et al. |
| D449,692 S | 10/2001 | Michelson |
| 6,296,647 B1 | 10/2001 | Robioneck et al. |
| 6,302,883 B1 | 10/2001 | Bono |
| 6,306,136 B1 * | 10/2001 | Baccelli .................... 606/61 |
| 6,328,738 B1 | 12/2001 | Suddaby |
| 6,342,055 B1 | 1/2002 | Eisermann et al. |
| 6,355,036 B1 | 3/2002 | Nakajima |
| 6,383,189 B1 | 5/2002 | Schumacher |
| 6,395,030 B1 | 5/2002 | Songer et al. |
| 6,402,756 B1 | 6/2002 | Ralph et al. |
| 6,406,478 B1 | 6/2002 | Kuo |
| 6,410,519 B1 | 6/2002 | Gruskin et al. |
| 6,413,259 B1 | 7/2002 | Lyons et al. |
| 6,471,706 B1 | 10/2002 | Schumacher et al. |
| 6,503,250 B2 | 1/2003 | Paul |
| 6,533,786 B1 | 3/2003 | Needham et al. |
| 6,558,686 B1 | 5/2003 | Darouiche |
| 6,576,017 B2 | 6/2003 | Foley et al. |
| 6,585,738 B1 | 7/2003 | Mangione et al. |
| 6,602,256 B1 | 8/2003 | Hayes |
| 6,605,090 B1 | 8/2003 | Trieu et al. |
| 6,645,208 B2 * | 11/2003 | Apfelbaum et al. .......... 606/61 |
| 6,652,525 B1 | 11/2003 | Assaker et al. |
| 6,702,817 B2 | 3/2004 | Beger et al. |
| 6,764,489 B2 | 7/2004 | Ferree |
| 6,786,910 B2 | 9/2004 | Cohen et al. |
| 6,793,658 B2 | 9/2004 | LeHuec et al. |
| 6,855,147 B2 | 2/2005 | Harrington, Jr. |
| 6,872,210 B2 | 3/2005 | Hearn |
| 6,908,469 B2 | 6/2005 | Sellers et al. |
| 7,112,202 B2 | 9/2006 | Michelson |
| 7,115,130 B2 | 10/2006 | Michelson |
| 7,118,573 B2 * | 10/2006 | Michelson .................... 606/71 |
| 2001/0049559 A1 | 12/2001 | Koo et al. |
| 2002/0004660 A1 | 1/2002 | Henniges et al. |
| 2002/0055741 A1 | 5/2002 | Schlapfer et al. |
| 2002/0111630 A1 | 8/2002 | Ralph et al. |
| 2003/0229348 A1 | 12/2003 | Sevrain |
| 2004/0167521 A1 | 8/2004 | De Windt |
| 2005/0187554 A1 | 8/2005 | Michelson |
| 2005/0192576 A1 | 9/2005 | Michelson |
| 2005/0216010 A1 | 9/2005 | Michelson |

FOREIGN PATENT DOCUMENTS

| | | |
|---|---|---|
| DE | 4409833 | 10/1995 |
| DE | 4414781 | 11/1995 |
| DE | 19542064 | 6/1997 |
| WO | WO94/26193 | 11/1994 |

| | | |
|---|---|---|
| WO | WO95/35067 | 12/1995 |
| WO | WO96/08206 | 3/1996 |
| WO | WO96/039975 | 12/1996 |
| WO | WO99/56653 | 11/1999 |
| WO | WO 00/01314 | 1/2000 |
| WO | WO 01/26566 | 4/2001 |
| WO | WO 01/89428 | 11/2001 |
| WO | WO 02/085226 | 10/2002 |

OTHER PUBLICATIONS

Brochure by SYNTHES Spine for *Cervical Spine Locking Plate*; 1991.
ORION Brochure; *Anterior Cervical Plate System, Surgical Technique*, as described by Gary L. Lowery, M.D., Ph.D.; 1996.
CODMAN Brochure: *Anterior Cervical Plate System*; Sep. 1995.
EBI Brochure: *Introducing EBI VueLock, Anterior Cervical Plate System*; 2001.
Advertisement for Codman Anterior Cervical Plate System by Codman; Johnson & Johnson; Professional, Inc.; Sep. 1995.
Spinal Concepts Brochure: The Acufix, Anterior Cervical Plate System; prior to Jun. 4, 2002.
Blackstone Brochure: *Blackstone Anterior Cervical Plate*; prior to Jun. 4, 2002.
Alphatec Manufacturing Brochure: *Deltaloc, Anterior Cervical Plate System*; prior to Jun. 4, 2002.
Sofamor Danek Brochure: *Atlantis, Anterior Cervical Plate System*; 1998.
Ortho Development Brochure: *Ortho Development Cervical Plate*; prior to Jun. 4, 2002.
Osteotech Brochure: *Affirm, Anterior Cervical Plate System*; prior to Jun. 4, 2002.
Bone Growth Stimulation, http://www.healthatoz.com/healthatoz/Atoz/ency/bone_growth_stimulation.isp.; prior to Jun. 4, 2002.

* cited by examiner

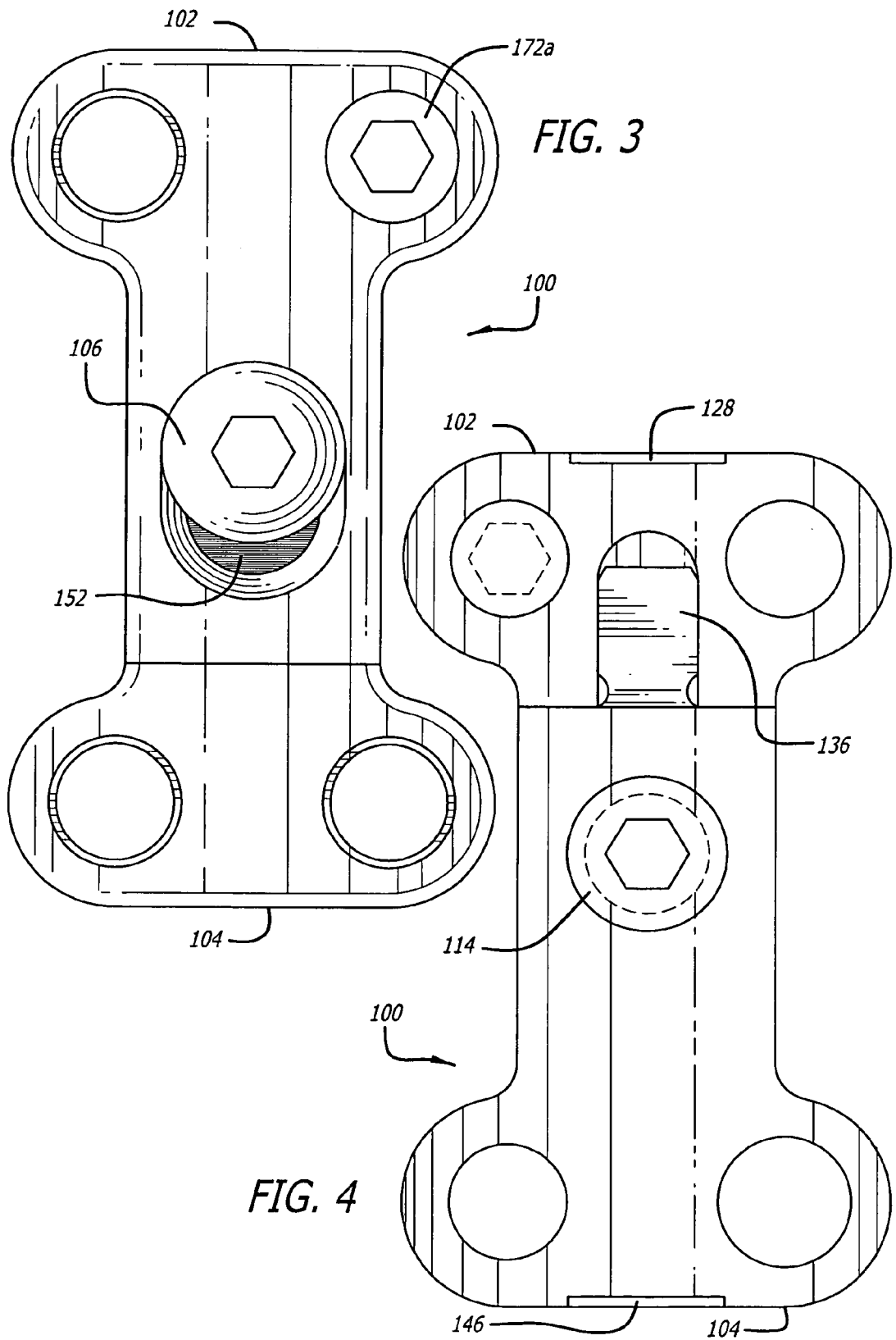

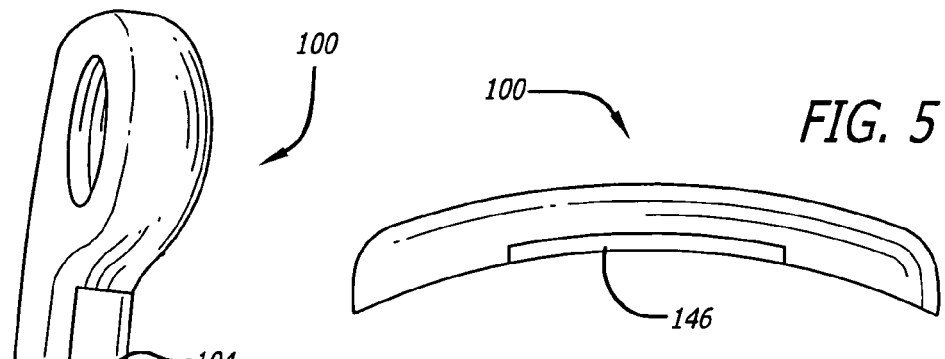
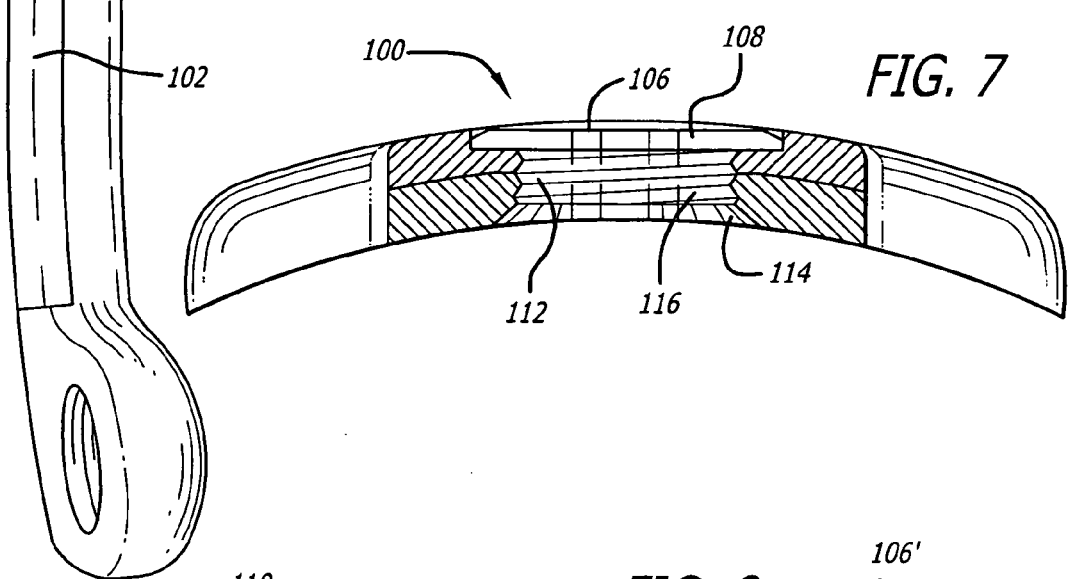
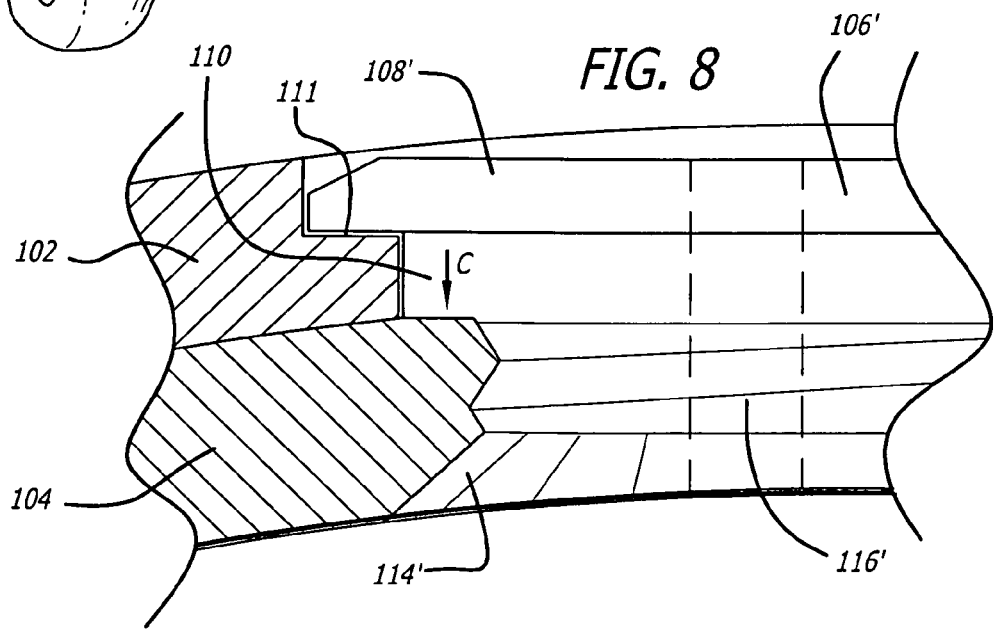

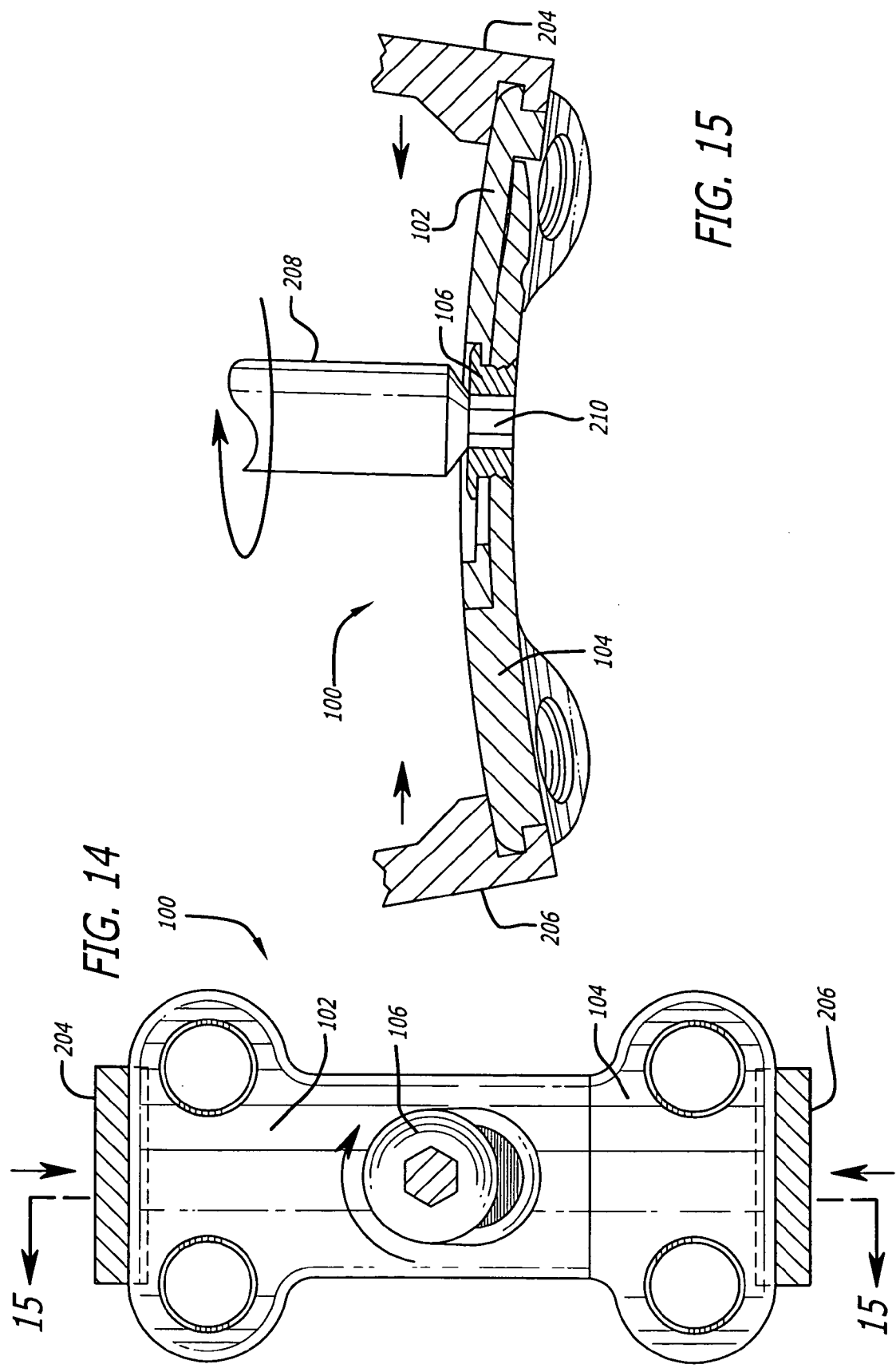

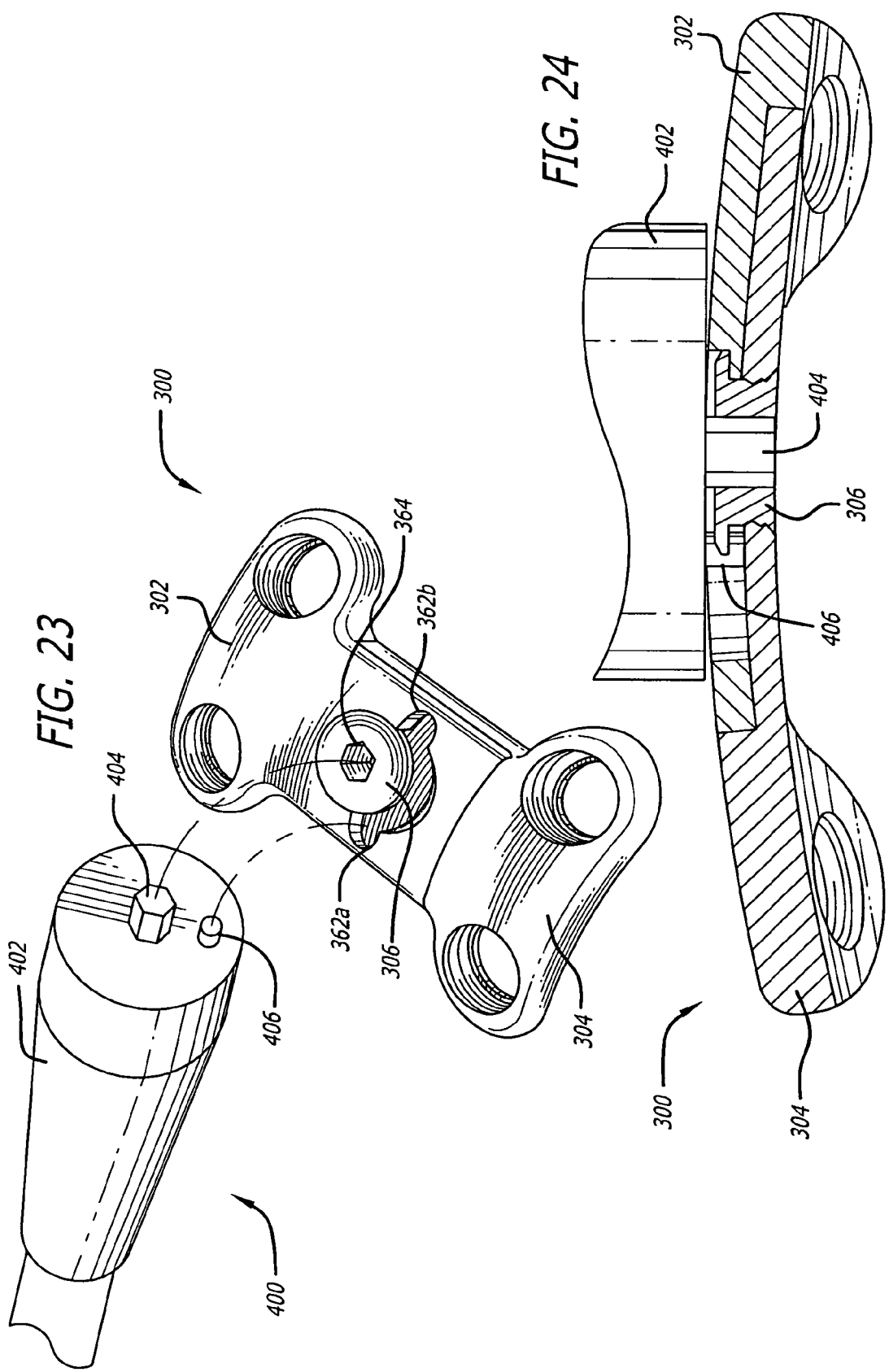

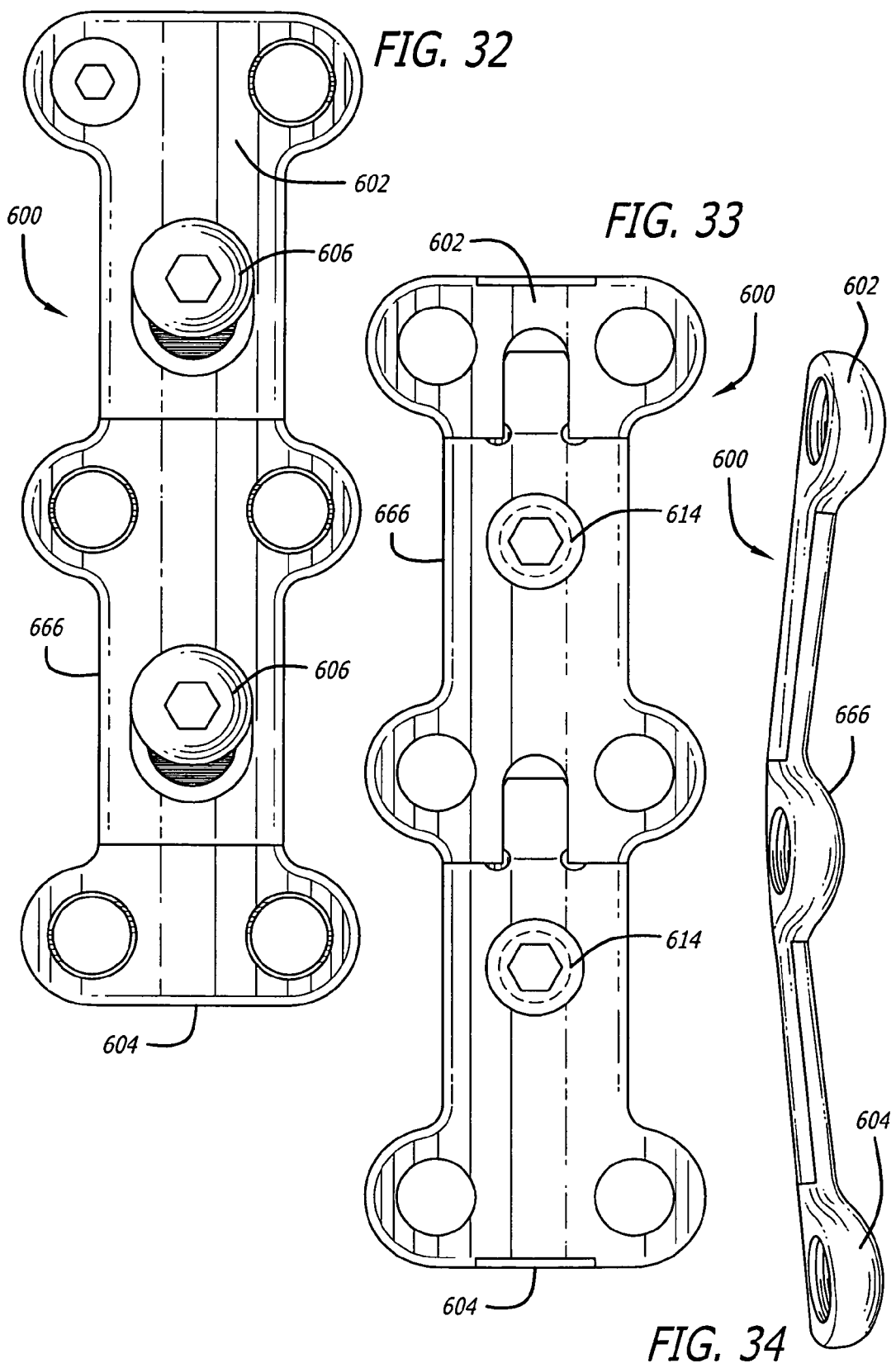

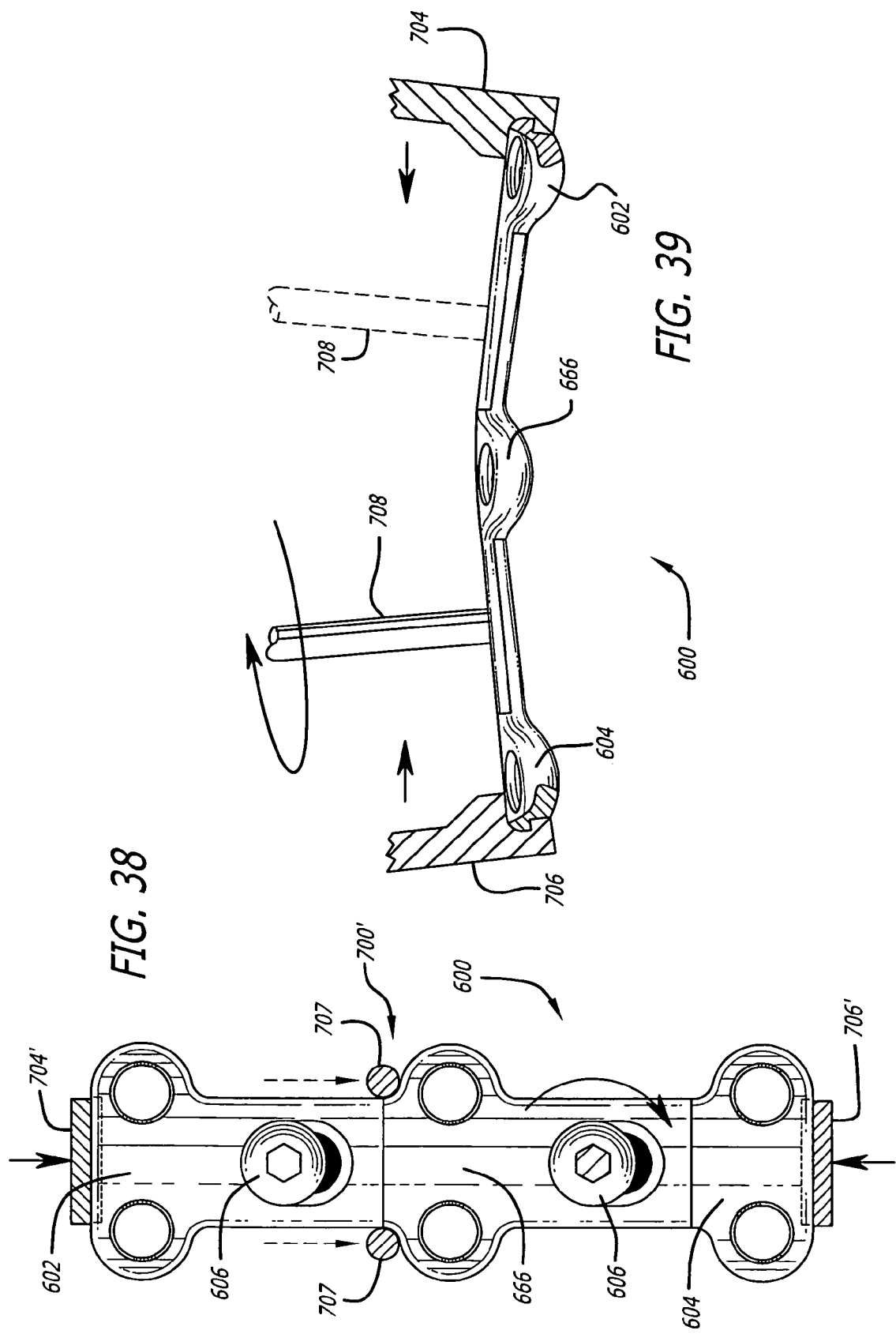

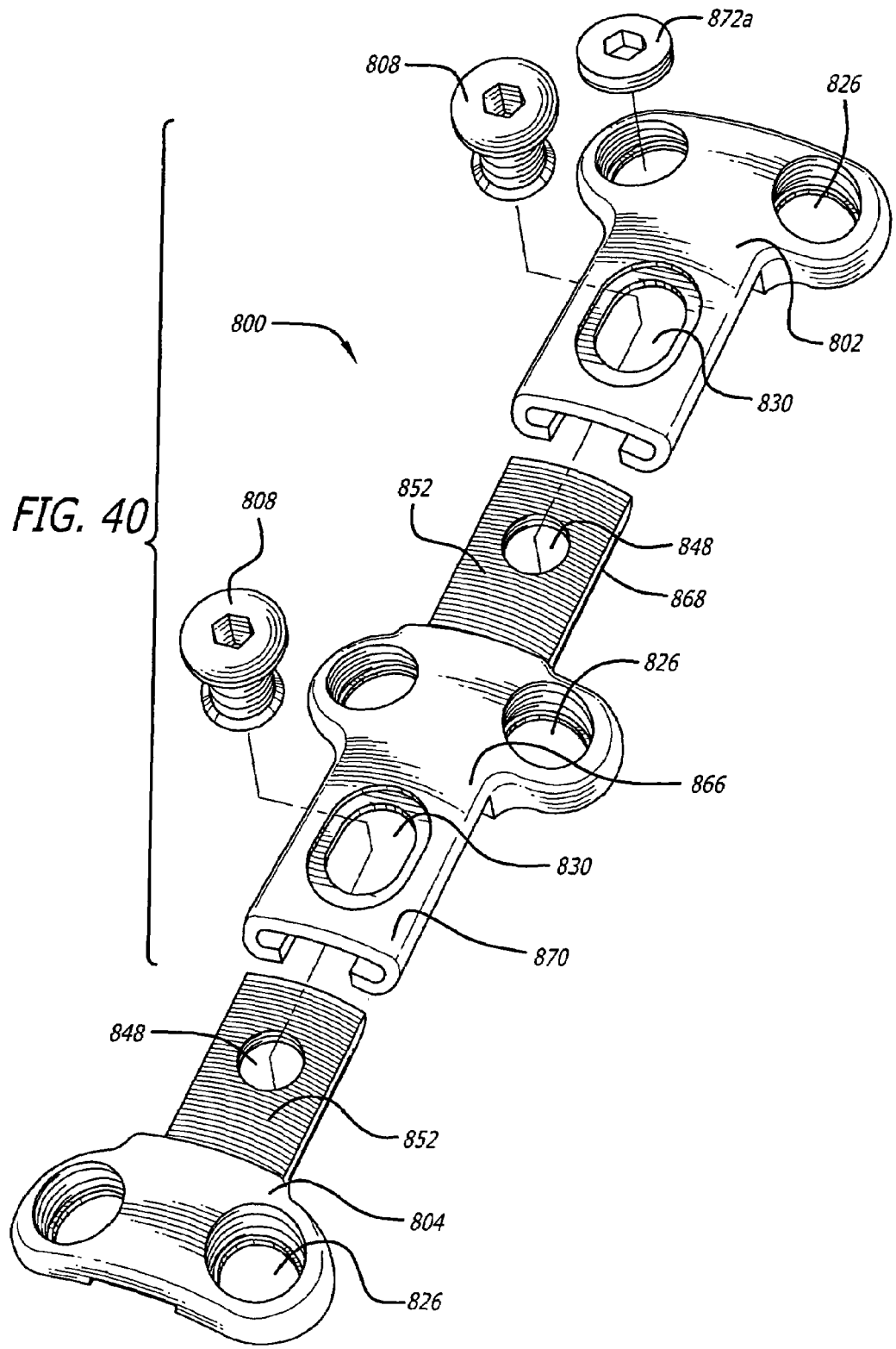

INSTRUMENTATION FOR USE WITH DYNAMIC SINGLE-LOCK ANTERIOR CERVICAL PLATE SYSTEM HAVING NON-DETACHABLY FASTENED AND MOVEABLE SEGMENTS

RELATED APPLICATIONS

This application is a divisional of U.S. application Ser. No. 10/160,086, filed Jun. 4, 2002 now U.S. Pat. No. 7,097,645, which claims the benefit of provisional Application No. 60/296,059, filed Jun. 4, 2001, and provisional Application No. 60/356,318, filed Feb. 12, 2002; all of which are incorporated by reference herein.

BACKGROUND

The use of plates, screws, and locks to prevent separation and backing out of screws from the plate, for use on the anterior aspect of the cervical spine to provide alignment and stability as an adjunct to fusion of adjacent vertebral bodies is known in the art. Also known in the art is that compressive load, within a physiological range across a fusion site, is beneficial to the fusion process. Conversely, a failure to maintain a compressive load across a fusion site, or to have a gap in the fusion construct continuity may lead to a failure to achieve fusion called pseudoarthrosis. A primary purpose of the aforementioned cervical hardware is to provide stability during the healing and fusion process. The fusion process occurs in part through a process called "creeping substitution" by which new living bone replaces the dead bone such as that of a bone graft. The fusion process involves a phase of bone resorption as preliminary to the formation of the new bone. It is possible then for the bone resorption to result in gaps in the continuity of the fusion mass, such that if the hardware is sufficiently rigid, such as occurs as a result of increasing the strength of the components and constraining the relationship of the screws to the plate, those gaps may persist and increase in size as the hardware holds the bone portions separated rather than allowing those bone portions to move together to close those gaps. This holding apart of the bone portions (called distraction) can therefore lead to a failure of fusion (pseudoarthrosis). These rigid systems by a combination of not inducing compression at the fusion site and of holding the bone portions to be fused apart may cause a "distraction pseudoarthrosis."

Alternative cervical plating systems have attempted to prevent distraction pseudoarthrosis by allowing the vertebral bodies to collapse towards each other as needed during the fusion process. Generally this has been done by allowing the bone screws to be free to move relative to the plate, that is, movement such as sliding, swiveling, rotating, and angulating, independent of whether the screws are prevented from separating or backing out of the plates such as by the use of locks. Undesired multidirectional instability can occur in such plating systems that is counter to the very purpose of such hardware which is to increase or provide for stability.

Another approach to solving this problem has been to attach by screws a block to each of the vertebral bodies to be fused and then to allow those blocks to slide up and down on a pair of rods. Each of these constructs have in common that they sacrifice stability, the ability to hold the bones to be fused rigidly in place and prevent undesired motion; for the ability to allow, but not cause the vertebral bodies to collapse.

There exists therefore a need for an improved anterior cervical plating system that is: (1) sufficiently rigid to maintain the desired alignment of the vertebral bodies to be fused; (2) capable of inducing compressive load across the fusion site; and/or (3) capable of allowing for the motion of the vertebral bodies towards each other to prevent or to close any gaps in the continuity of the fusion construct, while still being capable of preventing motion in all other directions. When similar challenges have been faced at other skeletal locations, the solution involved anchoring the bone screws through the far cortex of the bone portions to be joined, in effect anchoring the screws in such a way as to make it possible for the screws to force movement of the plates. In the cervical spine anteriorly, however, it has been found to be highly undesirable to drive the bone screws through the far cortex of the vertebral bodies, as this is where the spinal cord is located. There remains therefore a need for an improved cervical plating system as just described that does not require that the bone screws penetrate the far cortex to achieve the desired purpose as described.

The size of the vertebral bodies and the spacing between the vertebral bodies varies from patient to patient. The height of the vertebral bodies and the discs therebetween may vary level by level even in the same person. Thus, a plate of correct length does not necessarily have bone screw receiving holes correctly positioned to overlie the vertebral bodies in accordance with the spacing of the vertebral bodies to which the plate is to be applied. As a result, conventional plating systems of the past had to be manufactured in many different lengths and spacing configurations which were nevertheless fixed in an attempt to provide plates for many, though still possibly not all, of the various sizes and spacings of the vertebral bodies to which the plate was to be applied. For example, in a multi-segment plate the length of the plate would need to correspond to the overall length of the vertebral bodies to be joined and actual distances therebetween and the screw holes of the plate arranged to overlie the vertebral bodies. In order to cover the possible range of sizes, health care facilities would need to carry a large inventory of different sizes of plates, in some cases as many as sixty different sized plates would be needed. Such a large inventory is an expensive undertaking and still worse, facilities with a high caseload need to invest in more than one of each plate size to provide for the possibility of overlapping demand for the same plate size. Facilities with lower caseloads may find it prohibitively expensive to stock an inventory of plates sufficient to cover the range of possible sizes and thus might not be able to afford to stock a set at all or have less than all sizes of plates needed for all cases. Manufactures cannot afford to place a set of plates on consignment in facilities with low caseloads as the number of sales would not cover the carrying costs of the plates.

There exists therefore a need for an improved anterior cervical plating system that (1) allows for the overall adjustability of the length of the plate; (2) allows for variations in spacing between the bone screw receiving holes of the plate portions corresponding to the attachment point of the plate to the vertebral bodies; (3) reduces the requisite plate inventory; and (4) can avoid or prevent distraction pseudoarthrosis without itself introducing multidirectional instability.

SUMMARY OF THE INVENTION

The present invention is a dynamic anterior cervical plating system including a plate comprising segments in moveable relationship to each other adapted to allow for the overall adjustability of the length of the plate and for variations in the intersegmental spacing of the bone screw receiving holes, create and/or store a compressive load across a disc space between two adjacent vertebral bodies to be fused, and/or allow motion of the vertebral bodies toward each other to prevent or close gaps in the continuity of a fusion construct, while preferably preventing motion in all other directions when in use. As used herein, a spinal fusion segment is defined as two vertebral bodies with an intervertebral implant, made of bone or an artificial material, in the disc space therebetween. As used herein, a fusion construct is defined as a spinal fusion segment plus the hardware, such as a plate and screws for example.

The ability to permit the movement of adjacent vertebral bodies toward one another is referred to herein as "dynamization." Dynamization may be "passive" allowing the plate to shorten when a shortening force, such as a compressive load is applied. Dynamization may be "active" wherein the plating system stores energy to induce shortening of the fusion construct should the opportunity present. The present invention plating system may passively dynamize, actively dynamize, provide a combination of both, as well as convert and store certain compressive stresses encountered during the healing phase as will be more fully described herein.

The plate segments can also be moved to vary the spacing between the plate segments as well as the overall length of the plate so that the size of the plate may be adjusted to correspond to a range of sizes and spacing of the adjacent vertebral bodies to which the plate is being applied thereby greatly reducing the inventory of plate sizes needed. The moveable plate segments combine to form the plate. Each plate segment is attached to a vertebral body to be fused by at least one bone screw and preferably a pair of bone screws, which when inserted, are preferably prevented from backing out of the plate by locking elements, one locking element per bone screw.

The paths of the bone screws through the plate may be fixed or variable. If the paths are variable, they may be more or less stable depending on how resistant to motion the screws are relative to the plate when the screws are locked to the plate. To the extent that screws are sufficiently stable in relation to the plate to make use of the present inventive teaching, these screw, plate, and lock combinations or variations thereon are also within the broad scope of the present invention.

In a first embodiment of the present invention, after each of the segments of the plate are attached to a respective one of the vertebral bodies to be fused, the plate is capable of movement from a first or elongated position to a second or shorter position, a process generally referred to as "passive dynamization"—that is the ability of the system to allow the plated spinal segment to shorten in response to unmet compressive loads to allow for the bone portions to be fused to move close together to restore contact. A preferred embodiment of this present invention is capable of allowing for this passive dynamization while preventing undesirable motions along and around all axes other than the motion along the longitudinal axis of the plate.

In another preferred embodiment of the present invention, the plate segments are articulated in such a way that even the one freedom of movement that is along the longitudinal axis of the plate is selectively limited to the desired passive dynamization—that is shortening of the plate construct. This preferred embodiment of the present invention will shorten as required to maintain loaded contact of the bone portions to be fused, and if challenged, resist any forces such as those that would accompany cervical extension that would distract or destabilize the construct by elongating it. A further benefit of this embodiment is its ability to store and impart a compressive load across the fusion site referred to herein as "active dynamization" wherein energy stored in the system shortens the plate construct if conditions permit. This load can be applied by the surgeon at the time of surgery and/or be produced during the healing phase by harnessing the compressive loads such as occur randomly with neck motion. Compressive load within a physiological range has been shown to have a beneficial effect on the healing of bone. The induction of a compressive load across vertebral bodies to be fused, induces bone growth and when bone resorption occurs at the interface of the graft or implant and the vertebral bodies to be joined, those vertebral bodies are urged to move closer together, thus avoiding the formation of a gap therebetween and thereby acting to mitigate against pseudoarthrosis.

Alternatively, various embodiments of the present invention allow the surgeon to induce a desired amount of preload (compressive force) across the fusion site and to permit a desired amount of shortening of the construct—"active dynamization" should the opportunity occur; and yet lock the system to prevent any further shortening as might present a risk of deformity or be otherwise undesirable. Such a system urges the bone portions closer together.

In a preferred embodiment, a pre-load force can be applied to the plate segments such that while the plate segments may undergo no added motion initially, there is a selective force applied to the plate segments and the plate segments are capable of motion in only one direction, such that should resorption occur at one of the fusion interfaces then the plate segments are not only free to move in a direction toward one another, and only in that direction, but are also urged to do so to relieve that preload force. Such a system urges the vertebral bodies together over time as resorption permits.

Alternatively, in another embodiment of the plate of the present invention, a desired amount of preload (compressive force) may be induced across the fusion site to permit active dynamization should the opportunity occur, without locking the system such that after active dynamization is exhausted (if exhausted), then the plate will still allow passive dynamization to occur thereafter.

In another embodiment of the present invention, the plate includes a structural feature such as a groove, recess, slot, cam, or pivot, within its physical perimeter to engage a tool to cooperatively move segments of the plate towards each other. These embodiments of the present invention may be adapted to allow for passive, active, or active plus passive dynamization, and when used to store compressive load to allow for or prevent further motion thereafter. In a preferred version of the this embodiment, the structural feature contained within the plate for generating the compressive load and/or shortening the plate, may also serve as the locking mechanism to limit the amount of further shortening possible.

Various embodiments of the plating system of the present invention provide one or more of the following advantages:

1. Reduces the requisite plate inventory as each plate may cover a range of sizes. The plate may have its segments moved relative to one another so that the spacing between the plate segments may be adjusted so as to correspond to the actual distances between the vertebral bodies to be fused in a multi-segment construct for a more precise fit. The height of the discs and the vertebral bodies may vary level by level even in the same person. Thus, the ability to adjust the distances between the segments of the plates that correspond to the attachments to those vertebral bodies allows for a more precise fit of the plate to the spine with a reduced inventory of the number of plates required to do so.

2. It is possible to precisely contour each segment separately.

3. Reduces the risk that the plate construct will be discovered to be too short or too long after the attachment process has commenced.

4. It is possible to compress and dynamize levels selectively.

5. The fasteners that link the segments can be tightened to lock the segments after they are compressed or, alternatively, can allow for further motion of the plate segments together.

6. The same hardware can provide for passive dynamization or be rigidly fixed depending on the fasteners used to link plate segments.

7. The system can allow for passive dynamization, active dynamization, the combination of passive and active dynamization, or can convert body motion into active dynamization.

BRIEF DESCRIPTION OF THE DRAWINGS

FIG. 3 is a top plan view of the plate, fastener, and locking element of FIG. 1.

FIG. 4 is a bottom plan view of the plate, fastener, and locking element of FIG. 1.

FIG. 5 is an end view of the plate of FIG. 1.

FIG. 6 is a side elevation view of the plate of FIG. 1.

FIG. 7 is a partial cross sectional view of the plate of FIG. 1.

FIG. 8 is an enlarged fragmentary view of the plate of FIG. 1 and an alternative embodiment of a fastener in accordance with the present invention.

FIG. 14 is a top plan view of the plate and fastener of FIG. 1 in a compressed state with the instrumentation of FIG. 13 shown in cross section engaging the ends of the plate to compress the plate in the direction of the arrows and with the instrumentation engaging the fastener.

FIG. 15 is a partial cross sectional view along line 15-15 of FIG. 14.

FIG. 23 is a top plan view of the plate and fastener of FIG. 16 and a partial fragmentary perspective view of an instrument for compressing the plate and securing the fastener in accordance with another preferred embodiment of the present invention.

FIG. 24 is an enlarged cross sectional view of the plate of FIG. 16 with the instrument of FIG. 23 engaging the fastener and positioned within the plate.

FIG. 32 is a top plan view of the plate, fasteners, and locking element of FIG. 29.

FIG. 33 is a bottom plan view of the plate, fasteners, and locking element of FIG. 29.

FIG. 34 is a side elevation view of the plate of FIG. 29.

FIG. 38 is a top plan view of the plate of FIG. 29 in a compressed state with the instrumentation of FIG. 37 shown in cross section engaging the ends of the plate to compress the plate in the direction of the arrows, an alternative embodiment of instrumentation for engaging an intermediary portion of the plate to compress the plate in the direction of the arrows in dotted line, and instrumentation engaging the fastener and positioned within the plate.

FIG. 39 is a side elevation view of the plate of FIG. 38 with the instrumentation shown in partial fragmentary, hidden line, and cross sectional views.

FIG. 40 is an exploded top perspective view of a plate, fasteners, and locking element in accordance with another preferred embodiment of the present invention.

DETAILED DESCRIPTION OF THE DRAWINGS

Figure 1:
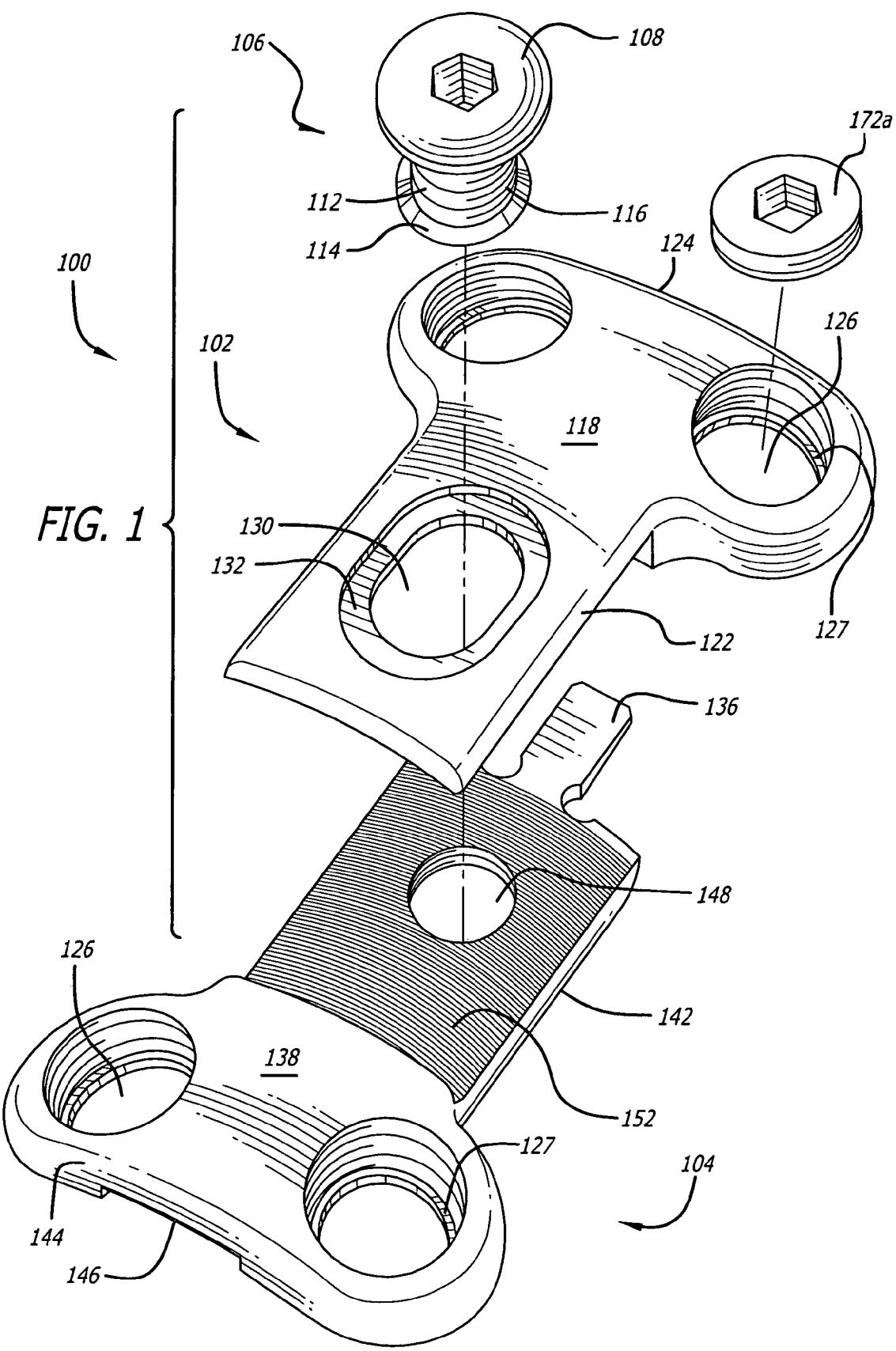
FIG. 1 is an exploded top perspective view of a plate, a fastener, and a locking element in accordance with a preferred embodiment of the present invention.

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

The present invention is for use in the cervical spine where dynamization is highly desired to prevent distraction pseudoarthrosis and to maintain a compressive load across the fusion interfaces. The present invention in one preferred embodiment is directed to a cervical plate generally having at least two movable segments that are attached to the vertebral bodies to be fused and connected in such a way as to permit dynamization of the vertebral bodies preferably along the longitudinal axis of the plate. The movement of the segments relative to one another may be accompanied by a reduction in the overall length of the plate.

FIGS. 1-7 show a preferred embodiment of a cervical plate 100 in accordance with the present invention. Plate 100 is preferably formed of a first segment 102 and a second segment 104 in moveable relationship to one another. First and second segments 102, 104 can be of various lengths and/or configurations such that when the segments are assembled preferably overlapping at least in part, plates of various lengths and/or configurations can be formed to cover a range of sizes. First and second segments 102, 104 can be of the same or different lengths and can be coupled to each other or to an intermediate segment as shown in FIGS. 29-40 and described below in connection with other preferred embodiments of the present invention. The overall length of plate 100 and the spacing of segments 102, 104 can be adjusted by moving segments 102, 104 relative to one another.

A non-detachable fastener 106 couples together first and second segments 102, 104. Fastener 106 is configured to be non-detachably attached to at least one of first and second segments 102, 104 to couple together two or more plate segments. Fastener 106 is non-detachable to prevent complete uncoupling of first and second segments 102, 104 from one another during normal use. As used herein, "non-detachable fastener" is defined as a fastener that once attached is not meant to be removed and then reattached. As shown in FIG. 7, fastener 106, for example, may be embodied in the form of a rivet having a head 108, a shaft 112, and a base 114. By way of example only and not limitation, base 114 may be coupled to second segment 104 so that it is permanently attached, but is still capable of an element of rotation about its longitudinal axis. Shaft 112 of fastener 106 preferably has a thread 116.

As shown in FIG. 8, in another preferred embodiment fastener 106' may be configured to be tightened to only one of first and second plate segments 102, 104 so as to permit movement of first and second segments 102, 104 relative to one another when fastener 106' is fully tightened. For example, fastener 106' may have a shoulder 110 adapted to bear upon second segment 104 as indicated by arrow C. Shoulder 110 is dimensioned so as to create a gap 111 between head 108' and first segment 102 so as to still permit a specific and desired motion of first and second segments 102, 104 relative to one another when fastener 106' is fully tightened. The limited motion of first and second segments 102, 104 relative to one another provides for dynamization of the spinal segment to be fused in that those vertebral bodies are allowed to move closer together to maintain contact.

Figure 2:
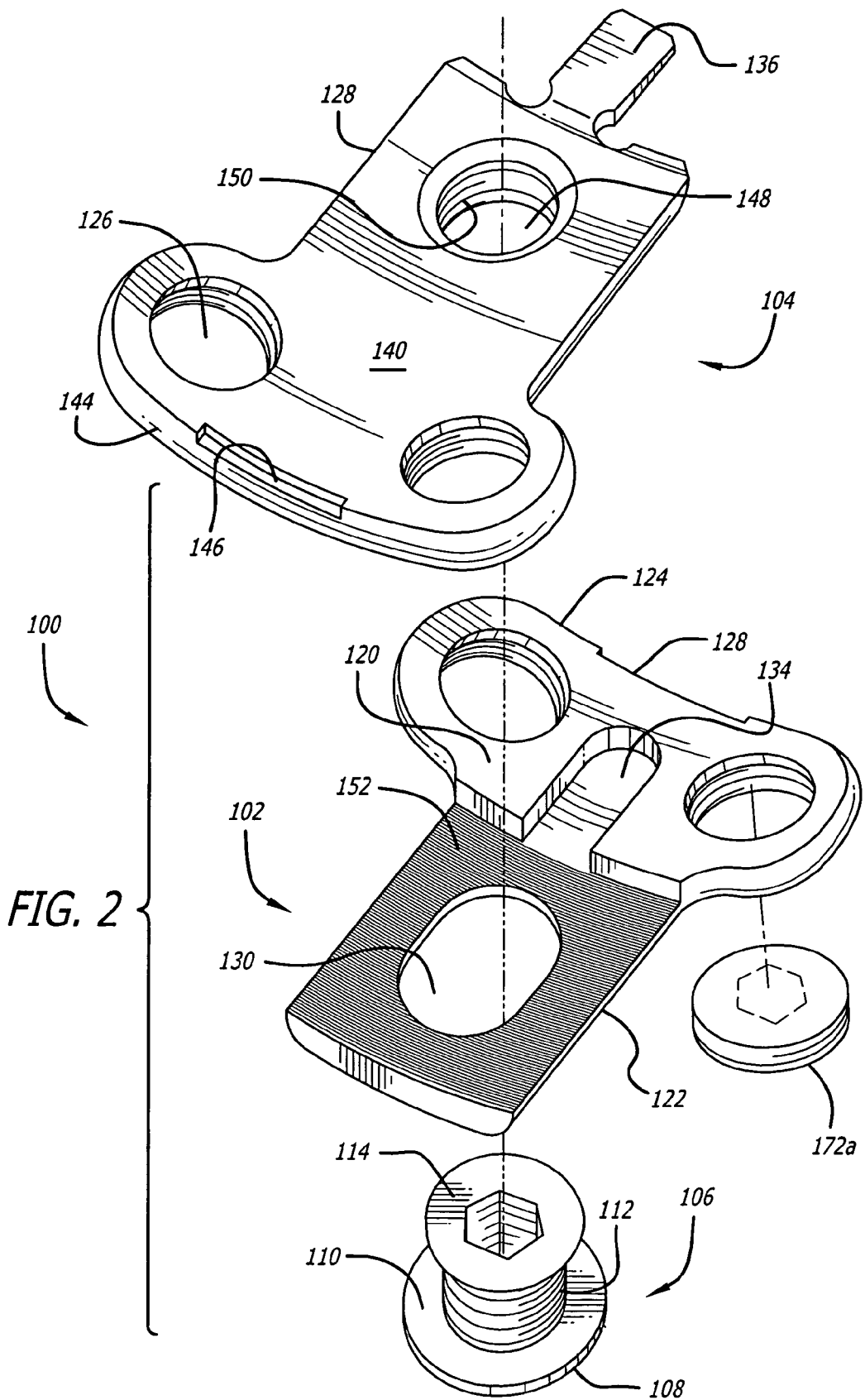
FIG. 2 is an exploded bottom perspective view of the plate, fastener, and locking element of FIG. 1.

As shown in FIG. 2, first segment 102 preferably has an upper surface 118, a lower surface 120, a medial portion 122, and an end 124. First segment 102 preferably includes bone screw receiving holes 126 proximate end 124. Bone screw receiving hole 126 is preferably configured to receive a single bone screw or the bone screw receiving holes also may be configured to receive more than one bone screw. By way of example only and not limitation, a bone screw receiving hole may be in the form of a slot sized to receive at least two bone screws.

Preferably, at least two of bone screw receiving holes 126 may be oriented in plate 100 to overlie the anterior aspect of a single cervical vertebral body adjacent a disc space to be fused, though the invention is not so limited. For example, a first pair of bone screw receiving holes 126 may be configured to overlie the anterior aspect of a first cervical vertebral body adjacent a disc space to be fused and at least a second pair of bone screw receiving holes 126 may be oriented in plate 100 to overlie the anterior aspect of a second cervical vertebral body adjacent the disc space to be fused.

Bone screw receiving hole 126 may, though need not be, configured to form an interference fit with at least a portion of the trailing end of a properly dimensioned bone screw to be received therein. Bone screw receiving holes 126 may be configured, for example only, so that at least one of bone screw receiving holes 126 may hold a bone screw in a fixed relationship to the plate or may hold a bone screw in a moveable relationship, such as a variable angular relationship, described below. By way of example only and not limitation, bone screw receiving hole 126 may have a reduced dimension proximate lower surface 120 of segment 102 to form a seat 127. Seat 127 may have a surface adapted to contact at least a portion of a bone screw inserted therein. The surface may be at least in part planar, at least in part curved, or have any other configuration suitable for contacting at least a portion of a bone screw.

End 124 of first segment 102 may also include a tool engagement area 128 adapted to cooperatively engage instrumentation for holding plate 100 and instrumentation for moving first and second segments relative to one another to induce a desired amount of compressive force across the fusion sites and to permit a desired amount of shortening of plate 100. Medial portion 122 preferably has a fastener receiving opening 130 adapted to accommodate fastener 106 to couple first and second segments 102, 104 to one another.

Fastener receiving opening 130 is preferably configured to permit selected movement of fastener 106 therein and to permit selected motion of first and second segments 102, 104 along the longitudinal axis of plate 100. Fastener receiving opening 130 may include a shoulder 132 recessed from upper surface 118 of first segment 102 adapted to contact the underside of head 108 of fastener 106 in the tightened position to prevent movement of first and second segments 102, 104 relative to one another. Alternatively, if a fastener 106' is used, shoulder 110 contacts second segment 104 and the underside of head 108' is positioned relative to shoulder 132 to permit movement of first and second segments 102, 104 relative to each other along the longitudinal axis of the plate when in the tightened position providing for dynamization of the vertebral bodies to be fused to occur, if needed. Fastener 106 and fastener receiving opening 130 cooperate to prevent complete uncoupling of first and second segments 102, 104 from one another. For example, fastener receiving opening 130 may be configured to prevent head 108 of fastener 106 from passing therethrough.

Lower surface 120 of first segment 102 includes a tab receiving recess 134 for receiving a tab 136 described below.

Second segment 104 has an upper surface 138, a lower surface 140, a medial portion 142, and an end 144. Second segment 104 preferably has bone screw receiving holes 126 proximate end 144. End 144 may also include a tool engagement area 146 adapted to cooperatively engage instrumentation for holding plate 100 and instrumentation for moving first and second segments 102, 104 relative to one another to induce a desired amount of compressive force across the fusion site and to permit a desired amount of shortening of plate 100. Medial portion 142 preferably includes a fastener receiving opening 148 for receiving a portion of fastener 106. Fastener receiving opening 148 is configured to permit non-detachable attachment of fastener 106 while permitting an element of rotation of fastener 106 about its longitudinal axis. For example, the bottom portion of fastener receiving opening 148 proximate lower surface 140 of second segment 104 may have a smaller dimension than the maximum dimension of base 114 (e.g. flared portion of a rivet) of fastener 106 so as to prevent passage of the end portion therethrough. Moreover, the bottom portion of fastener receiving opening 148 may be beveled to accommodate base 114 (e.g. flared portion) of fastener 106 so that it is generally flush or recessed to the bottom surface and preferably does not impede close contact of lower surface 140 with the surface of the vertebral bodies. The first and second plate segments may be modular components of various configurations assembled by the manufacturer of the plate and provided to the surgeon in an assembled state. In the assembled state, the plate has a non-detachable fastener that prevents complete uncoupling of the first and second segments during normal use.

Fastener receiving opening 148 preferably has a thread 150 adapted to engage with thread 116 of fastener 106. The threaded engagement of fastener 106 to fastener receiving opening 148 permits first segment 102 and second segment 104 to be attached to each other when fastener 106 is sufficiently rotated and tightened. As fastener 106 is rotated further, first and second segments 102, 104 are secured together and locked and do not move relative to each other. Alternatively, if fastener 106' shown in FIG. 8 is used in the tightened position, first and second segments 102, 104 are capable of moving relative to each other.

Lower surfaces 120, 140 of first and second segments 102, 104 are preferably at least in part concave along at least a portion of the longitudinal axis of the plate, may be biconcave at least in part, that is, concave along the longitudinal axis of plate 100 and concave transverse to the longitudinal axis of the plate, or may have any shape suitable for the intended purpose transverse to the longitudinal axis of the plate. A person skilled in the art will appreciate that plate 100 may be adapted for other curvatures or have no curvature without departing from the intended purpose within the broad scope of the present invention. Lower surfaces 120, 140 are preferably adapted to contact at least a portion of the vertebral bodies to be fused and may be configured to conform to the anterior aspect of at least a portion of the vertebral bodies.

Second segment 104 preferably includes a tab 136 extending from medial portion 142. Tab 136 is configured to cooperatively engage a tab receiving recess 134 in the lower surface 120 of first segment 102. Tab 136 acts as a spring to maintain first and second segments 102, 104 aligned along the longitudinal axis of plate 100. Tab 136 also functions to limit movement of first segment 102 in a direction transverse to the longitudinal axis of plate 100 to prevent end 124 from dropping down beyond a desired position. This limited movement of first segment 100 prevents medial portion 122 of first segment 102 from lifting away from medial portion 142 beyond a desired position, so that ratchetings 150 are not overly separated and rendered less effective as described in more detail below. It is appreciated that other configurations of segments 102, 104 are possible to hold apart segments 102, 104 and to limit movement of the segments in a direction transverse to the longitudinal axis of the plate. For example, the longitudinal curvatures of first and second segments 102, 104 can be slightly different to spring apart segments 102, 104. For example, the radius of curvature of the lower surface of segment 102 may be different that the radius of curvature of the upper surface of segment 104.

At least a portion of lower surface 120 of first segment 102 and upper surface 138 of second segment 104 are preferably configured to interdigitate with one another to permit selected adjustment of the length of plate 100. For example, lower surface 120 and upper surface 138 may include a surface configuration, such as ratchetings 152, configured to cooperatively interdigitate to permit selected and sequential movement along the longitudinal axis of plate 100. The ratchetings are preferably biased to allow movement in one preferred direction along the longitudinal axis of the plate so as to allow shortening of the plate and resist lengthening of the plate.

Figure 9:
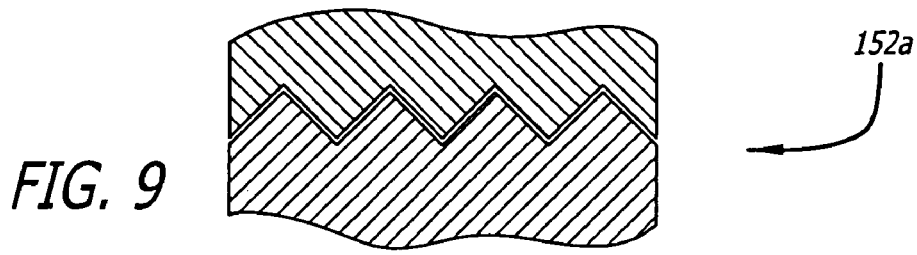
FIG. 9 is an enlarged fragmentary cross sectional view of an embodiment of the ratchetings in the upper and lower portions of the plate of FIG. 1 in a first position.
Figure 10:
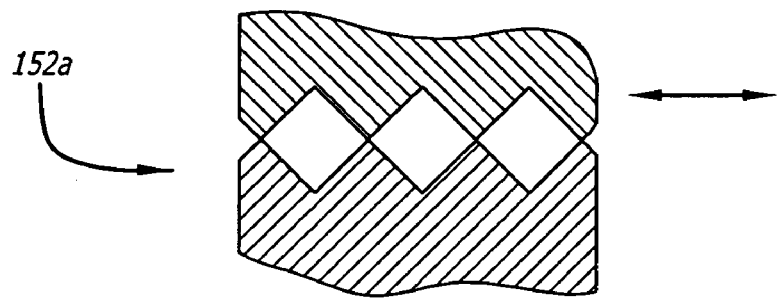
FIG. 10 is a fragmentary cross sectional view of FIG. 9 in a second position.

FIGS. 9 and 10 show an embodiment of ratchetings having a configuration that is useful if no movement of first and second segments 102, 104 is desired after fastener 106 is tightened. A preferred angular relationship of the cross section of ratchetings 152a is a 45-45-90 degree triangular relationship. As shown in FIG. 9, in a first position, the peaks and valleys of ratchetings 152a are cooperatively mating. Ratchetings 152a permit for the fixed positioning of first and second segments 102, 104 relative to one another to create a selected length of plate 100. As shown in FIG. 10, the peaks and valleys are separated to permit movement of the first and second segments in the directions of the arrows along the longitudinal axis of plate 100. In order for first and second segments 102, 104 to move relative to one another, there must be sufficient freedom of movement for the segments to move apart in order to clear the height of the peaks of ratchetings 152a. Accordingly, in a preferred embodiment fastener 106 is configured to have at least one position that permits movement of the first and second segments along the longitudinal axis of plate 100 as well as along an axis transverse to the longitudinal axis of plate 100 such that ratchetings 152 can move apart. Fastener 106 can be tightened to a second position to resist or prevent movement of segments 102, 104 relative to one another. For example, movement of segments 102, 104 can be resisted in a direction along at least a portion of the longitudinal axis of plate 100.

Figure 11:
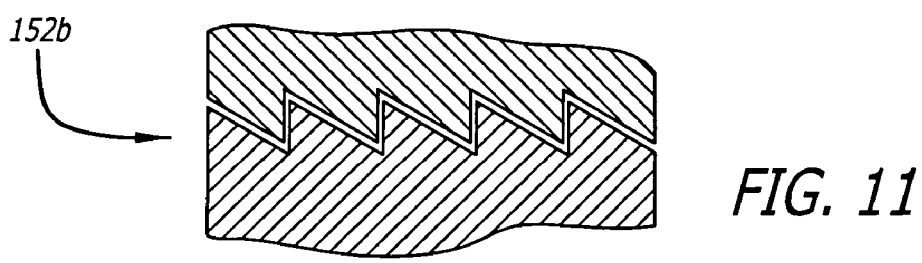
FIG. 11 is an enlarged fragmentary cross sectional view of a preferred embodiment of the ratchetings in the upper and lower portions of the plates of the present invention in a first position.
Figure 12:
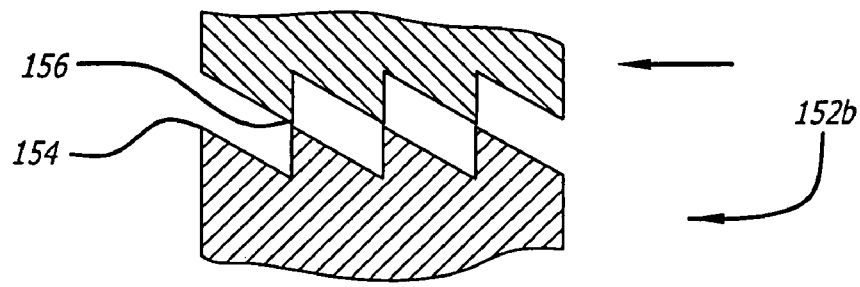
FIG. 12 is a fragmentary cross sectional view of FIG. 11 in a second position.

FIGS. 11 and 12 show another preferred embodiment of ratchetings 152b having a forward-facing configuration for permitting movement in a single direction. The configuration of ratchetings 152b is useful when movement of first and second segments 102, 104 is desired to permit further shortening of the plate. A preferred angular relationship of the triangular cross section of ratchetings 152b is a 30-60-90 degree triangular relationship. As shown in FIG. 12, due to the forward facing angle of ratchetings 152b, sliding movement of first and second segments 102, 104 in the direction, as indicated by the arrow, along the longitudinal axis of plate 100 is facilitated by the ramped surface 154. In contrast, sliding movement in the opposite direction is restricted by vertical wall 156. Movement of segments 102, 104 is limited to a single direction with ratchetings 152a and by limiting the separation of segments 102, 104 along an axis transverse to the longitudinal axis of plate 100 with fastener 106 or 106'.

In a preferred embodiment, fastener 106 or 106' is configured to have at least one position that permits movement of first and second segments 102, 104 in both directions along the longitudinal axis of plate 100 as well as along an axis transverse to the longitudinal axis of plate 100 such that ratchetings 152b can move apart. For example, in a first position fastener 106 can be less than fully tightened to plate 100 as desired by the surgeon to permit movement of first and second segments relative to each other. Fastener 106' can further have a second position that permits movement of segments 102, 104 relative to one another only in a single direction along the longitudinal axis of plate 100 and limits movement along an axis transverse to the longitudinal axis of plate 100. Therefore, plate 100 can be shortened if the distance between the two adjacent vertebral bodies decreases, even after plate 100 is installed, so that the vertebral bodies are not held apart by plate 100, to prevent the occurrence of pseudoarthrosis. One of the benefits of a forward-facing configuration of ratchetings 152b is the ability to store and impart a compressive load across the fusion site. The compressive load stored may be applied by the surgeon and/or compressive loads that occur randomly with neck motion during the healing phase. First and second segments 102, 104 may be pre-adjusted to correspond to the appropriate size and spacing of the adjacent vertebral bodies to be fused prior to placement of plate 100 against the vertebral bodies by moving first and second segments 102, 104 relative to one another while fastener 106 is only partially tightened for the purpose of appropriately adjusting the length of the plate. Then, fastener 106 may be further tightened to secure first and second segments 102, 104 in the desired position.

With appropriate embodiments of the plates described herein, the surgeon may induce a desired amount of "preload," or compressive force across the fusion site after plate attachment by moving first and second segments 102, 104 toward one another to shorten the length of plate 100 as desired. Inducing a preload enhances fusion by maintaining a compressive force between adjacent vertebral bodies and reducing the chance that gaps might develop as new living bone replaces the dead bone during the fusion process.

Figure 13:
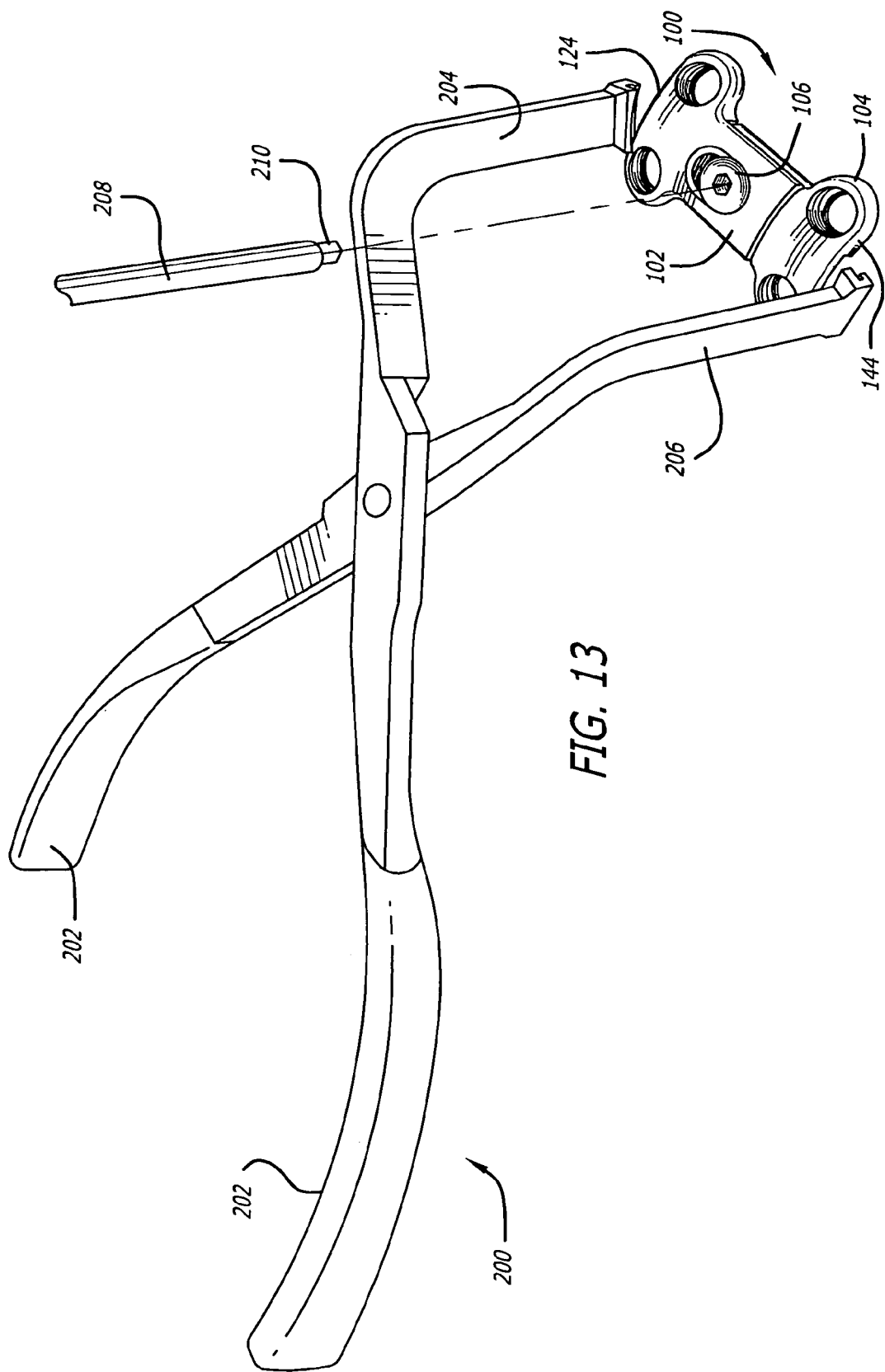
FIG. 13 is a top perspective view of the plate and fastener of FIG. 1 and instrumentation for compressing the plate and instrumentation for locking the fastener in accordance with a preferred embodiment of the present invention.
Figure 16:
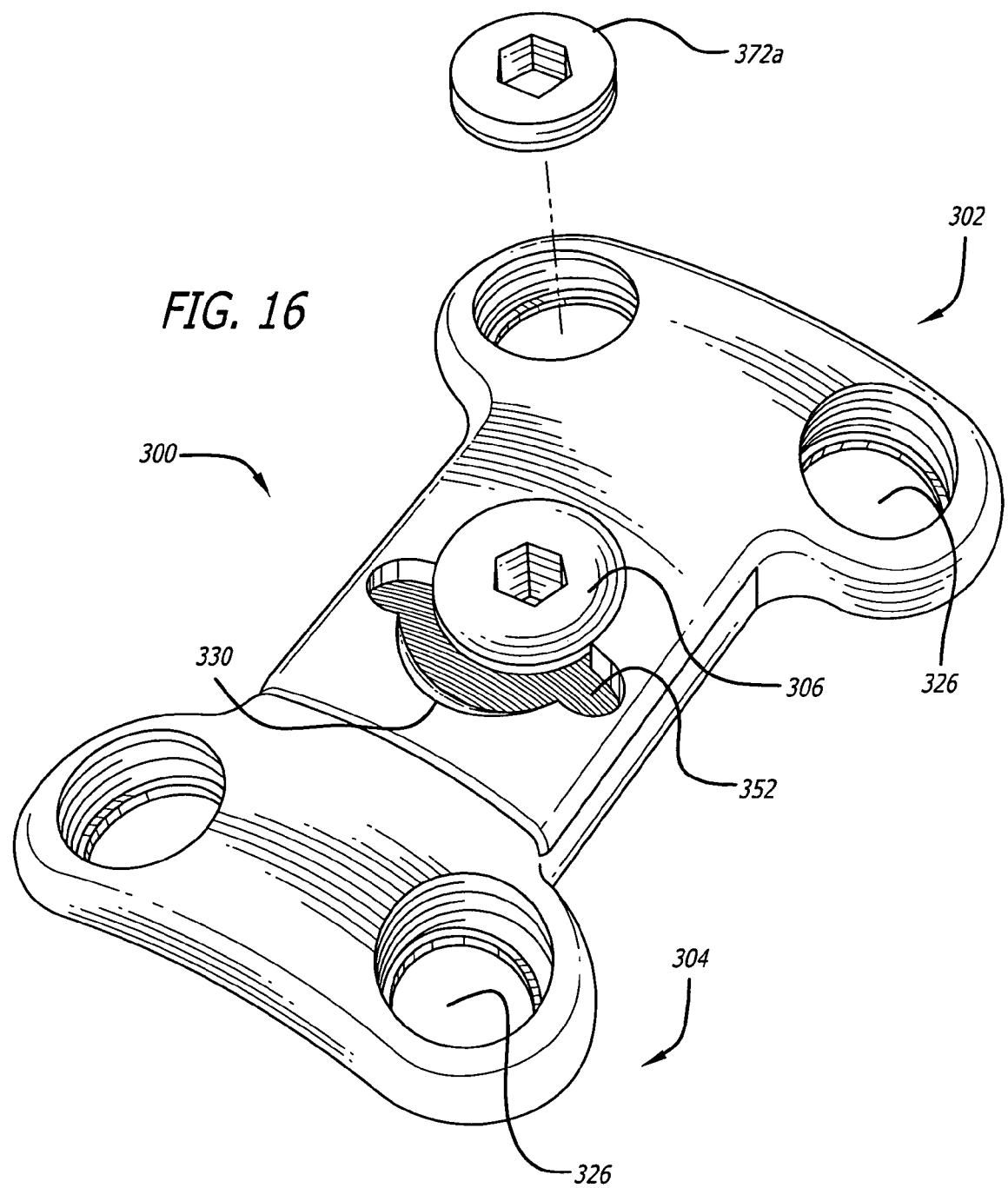
FIG. 16 is a top perspective view of a plate, a fastener, and a locking element in accordance with another preferred embodiment of the present invention.
Figure 17:
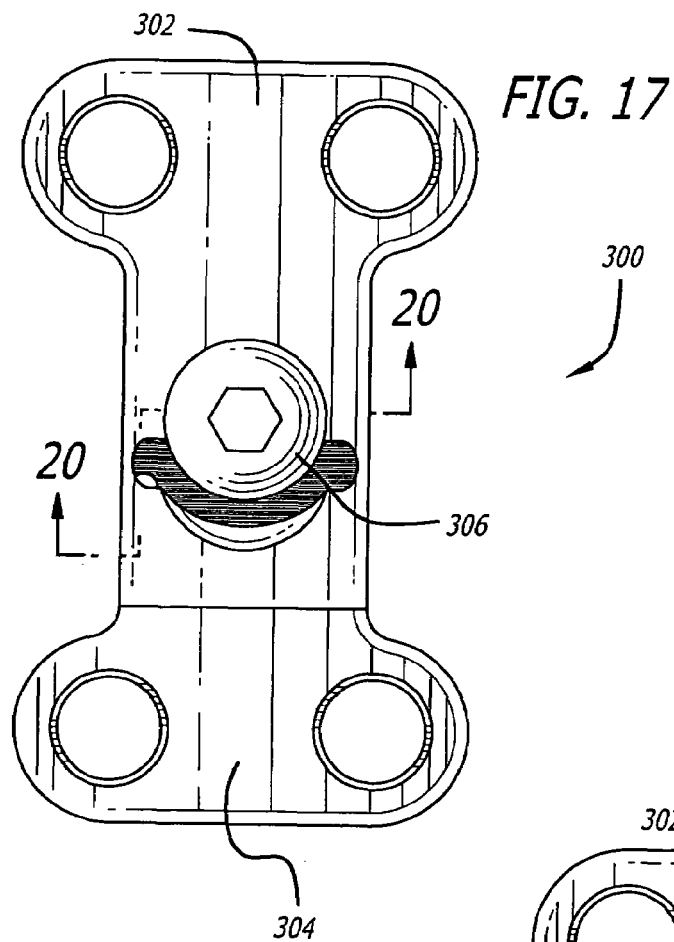
FIG. 17 is a top plan view of the plate and fastener of FIG. 16.
Figure 18:
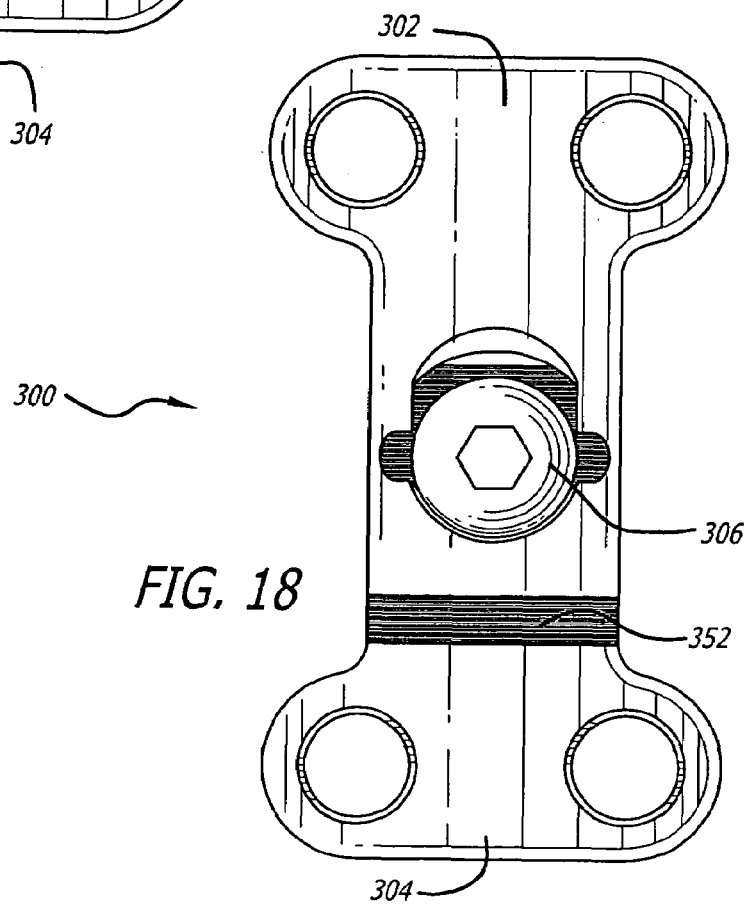
FIG. 18 is a top plan view of the plate of FIG. 16 in an elongated state and a fastener.
Figure 19:
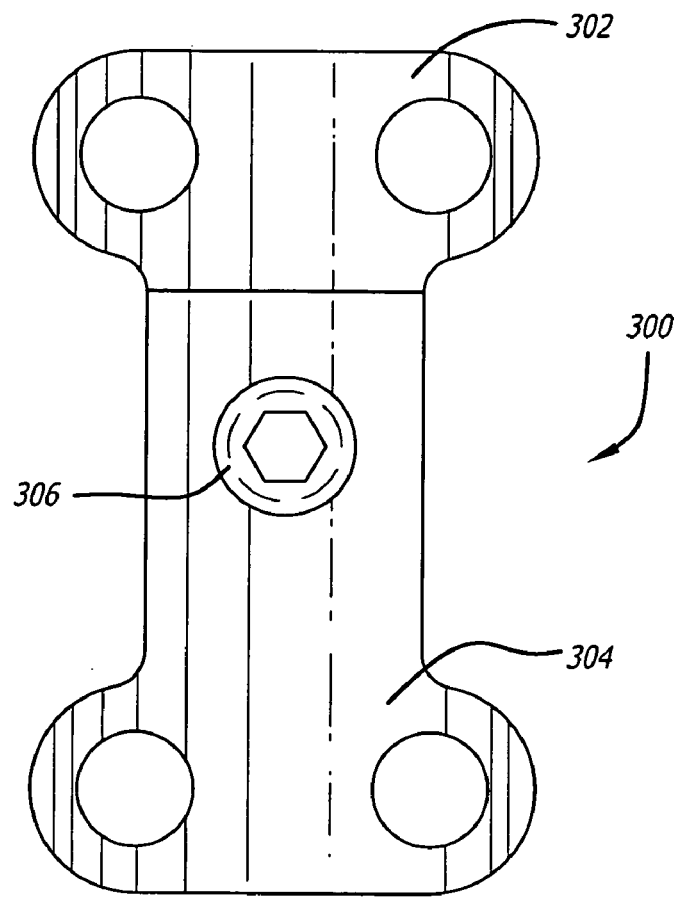
FIG. 19 is a bottom plan view of the plate and fastener of FIG. 16.

FIGS. 13-15 show a preferred embodiment of instrumentation 200 for compressing and locking plate 100. Instrumentation 200 has a handle 202 with a pair of tongs 204, 206 in a moveable relationship to each. Tongs 204, 206 are configured to cooperatively engage ends 124, 144 of first and second segments, 102, 104, respectively. Instrumentation 200 may be used to hold and position plate 100 in a desired position at the fusion site during at least a portion of the procedure for installing plate 100. Any instrument capable of engaging the plate so as to serve the intended purpose would be within the scope of the instrumentation and method of the present invention. As an example only, methods and instrumentation for installing plates to the cervical spine, including a pilot hole forming punch to create bone screw receiving holes in the vertebral bodies coaxially aligned with the bone screw receiving holes with the plate, are taught and described by Michelson in the U.S. Pat. No. 6,193,721 (the '721 patent), incorporated by reference herein. After segments 102, 104 have been attached to the adjacent vertebral bodies with an appropriate fastening element, such as bone screws, instrument 200 can be used to move segments 102, 104 toward one another to shorten the length of plate 100 and create a compressive load across the disc. space. After the desired length of plate 100 is achieved, an instrument 208 having a head 210 configured to cooperatively engage fastener 106 is used to tighten fastener 106 to secure first and second segments 102, 104 in a desired position. When in a secured position, segments 102, 104 may maintain a compressive load across the disc space if desired. Head 210 of instrument 208 may have a hex-shaped configuration.

FIGS. 16-22 show another preferred embodiment of a cervical plate 300 having an internal compression mechanism in accordance with the present invention. Plate 300 is similar to plate 100 except that fastener receiving opening 330 and fastener 306 function as part of a mechanism to move first and second segments 302, 304 relative to one another to change the length of plate 300 to generate a compressive load across the disc space between two adjacent vertebral bodies to be fused. Fastener receiving opening 330 includes instrument pin receiving recesses 362a and 362b for cooperating with the pin of an instrument 400 (described below) for moving first and second segments 302, 304 relative to one another. In addition, instead of a tab 136, plate 300 has pins 358 and tracks 360 to maintain first and second segments 302, 304 aligned along the longitudinal axis of plate 300.

Figure 20:
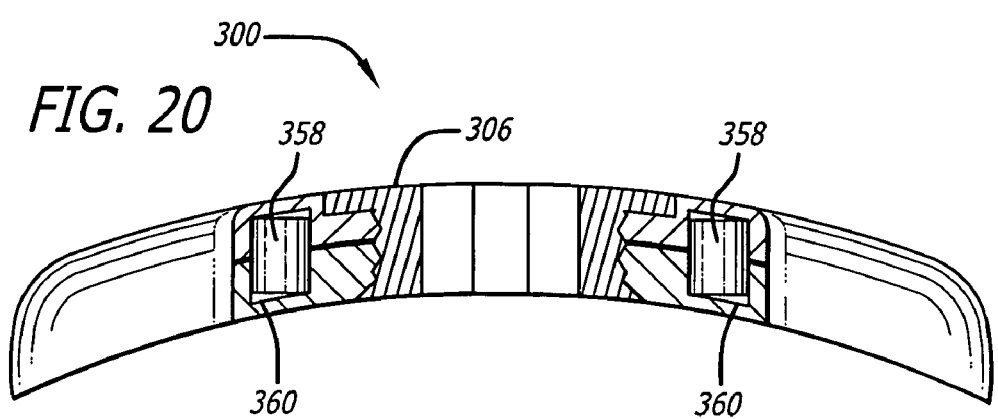
FIG. 20 is a partial cross sectional view along line 20-20 of the plate of FIG. 17.
Figure 21:
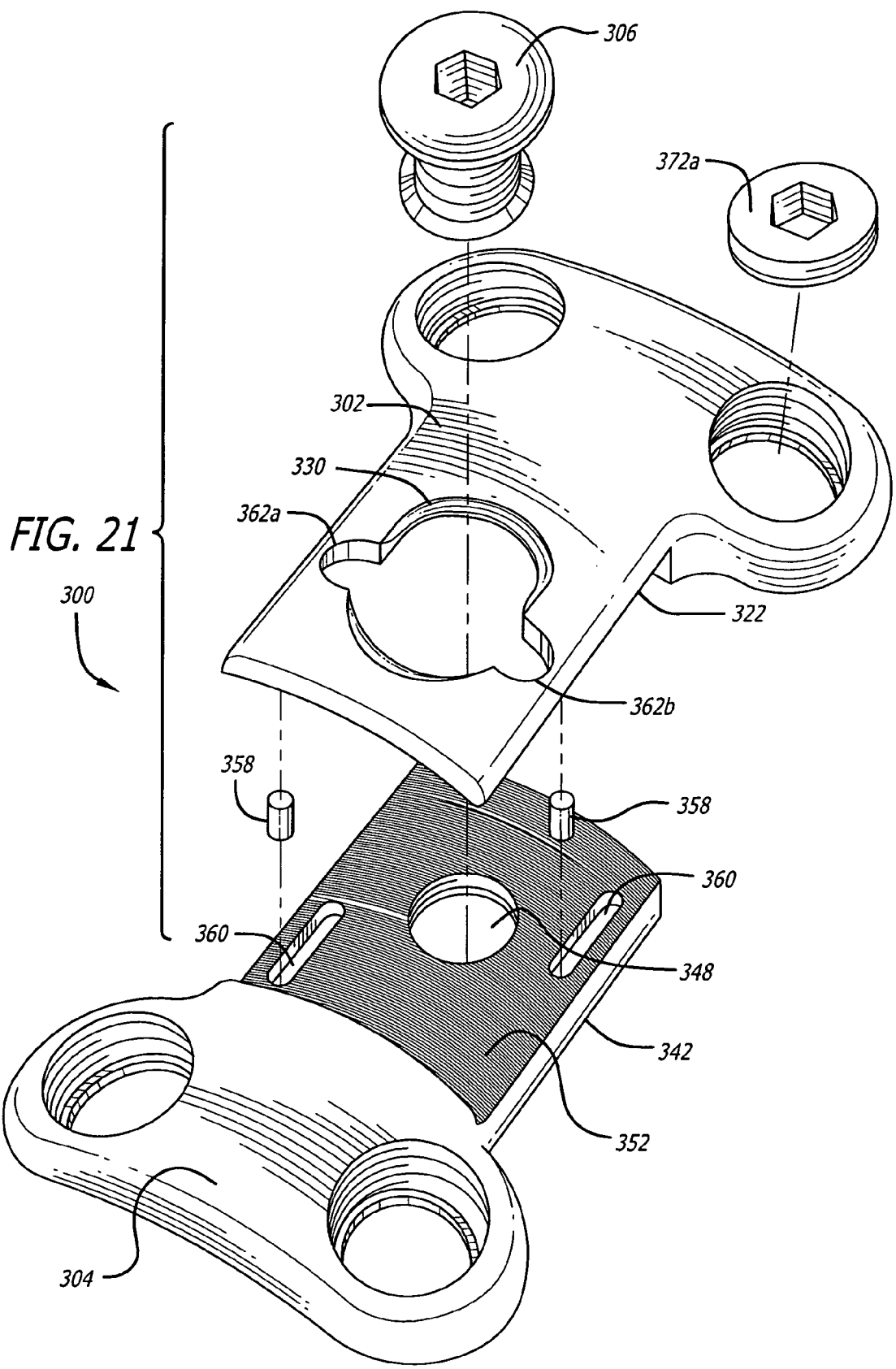
FIG. 21 is an exploded top perspective view of the plate, fastener, and locking element of FIG. 16.
Figure 22:
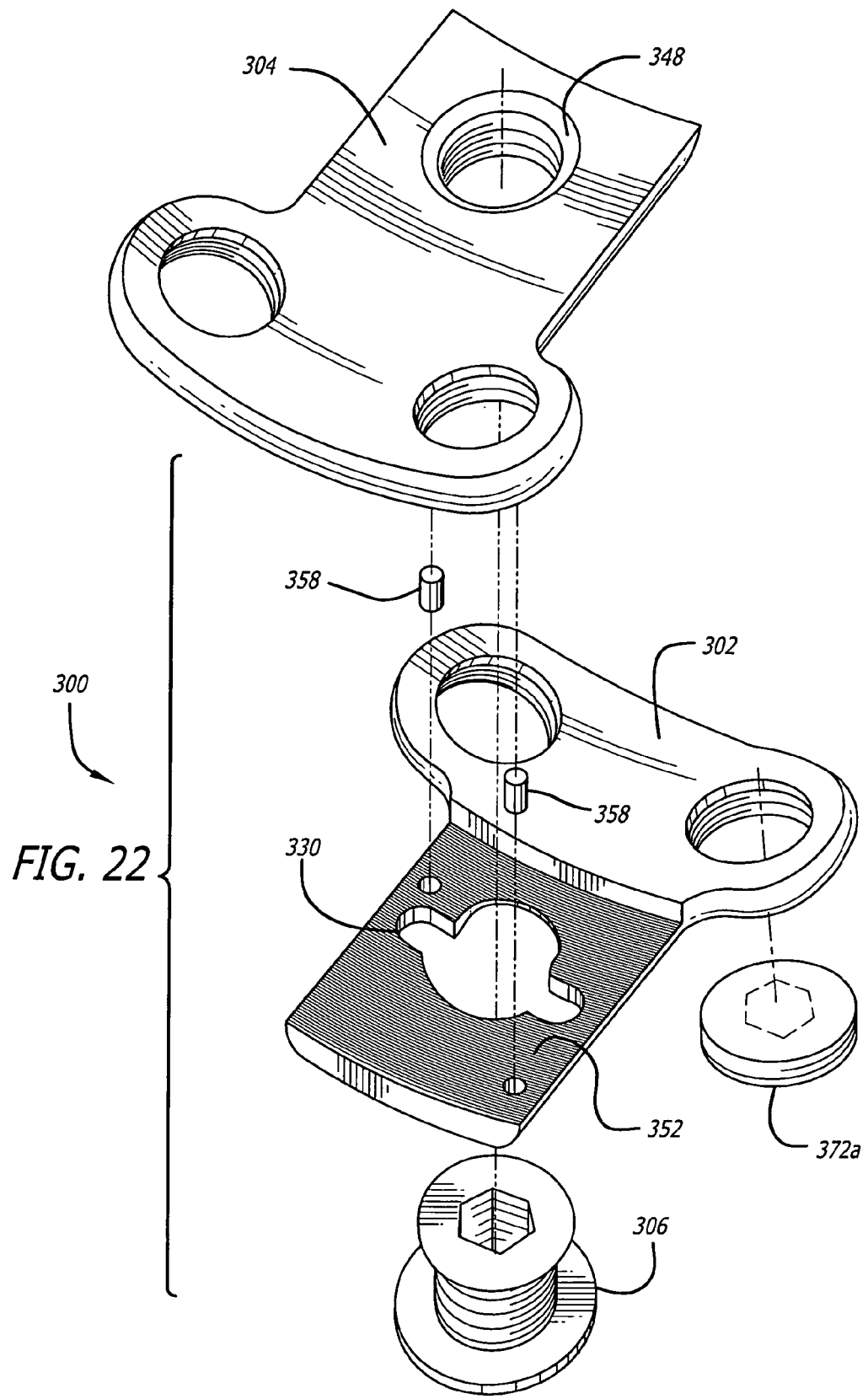
FIG. 22 is an exploded bottom perspective view of the plate and fastener of FIG. 16.

As shown in FIGS. 20-22, first segment 302 preferably has two pins 358 depending therefrom for engagement in corresponding tracks 360 in second segment 304. Pins 358 slideably engage tracks 360, respectively, and travel therein when first and second segments 302, 304 are moved relative to one another. Tracks 360 are staggered along the length of medial portion 342 and pins 358 are staggered along the length of medial portion 322 to maintain first and second segments 302, 304 aligned along the longitudinal axis of plate 300. It is appreciated that any plate configuration to achieve the intended purpose of maintaining first and second segments 302, 304 aligned along the longitudinal axis of the plate would be within the scope of the present invention.

Figure 25:
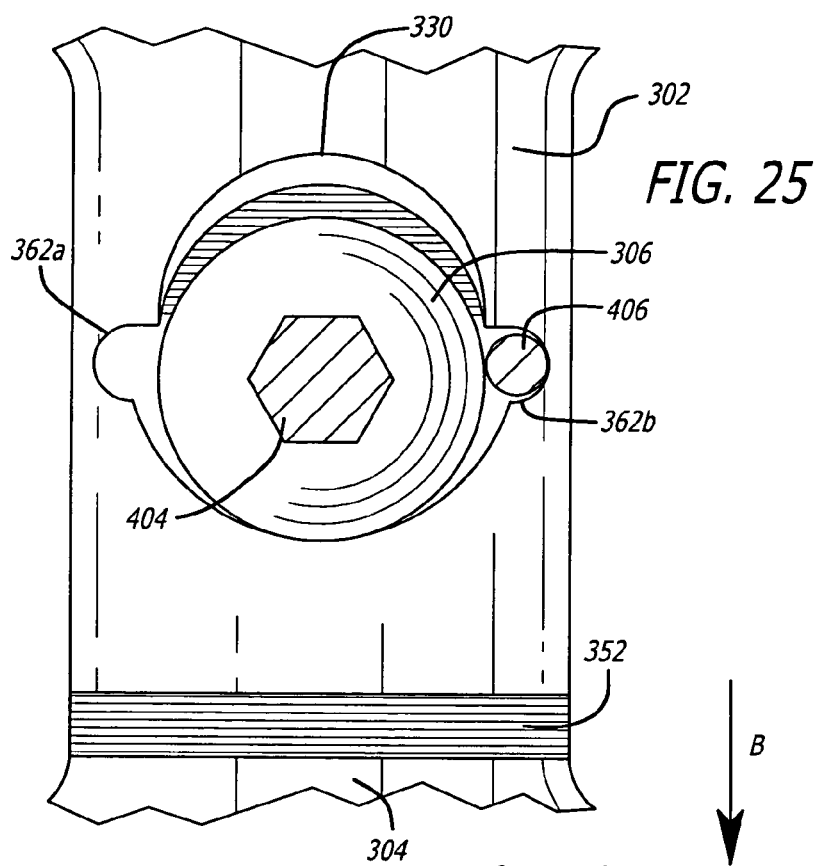
FIG. 25 is a fragmentary top plan view of the plate of FIG. 16 in an elongated state with the instrument of FIG. 23 shown in cross section engaging the fastener and positioned within the plate.
Figure 26:
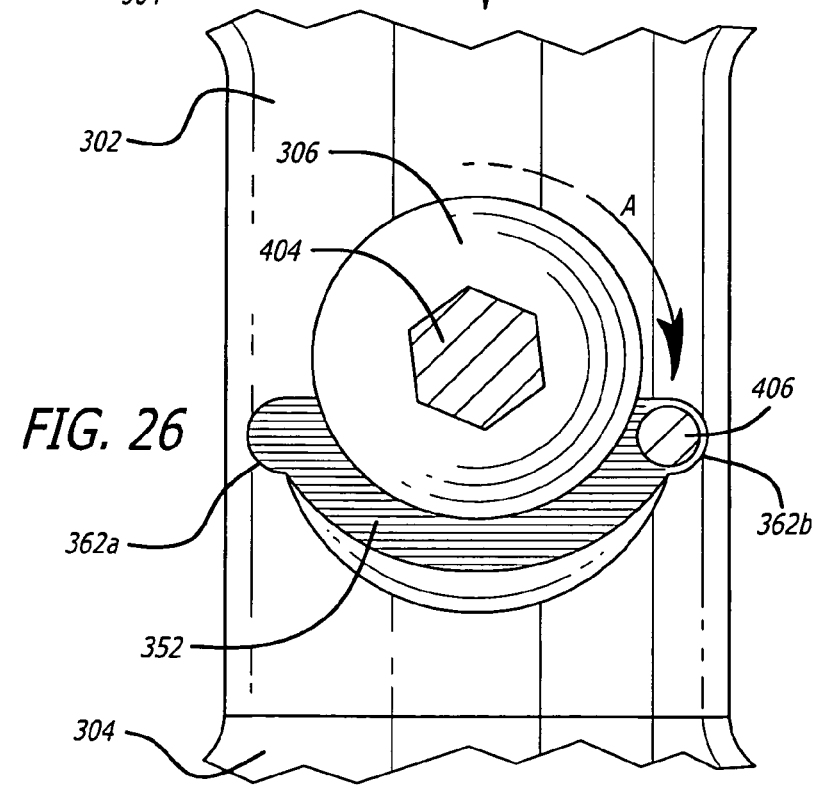
FIG. 26 is a fragmentary top plan view of the plate of FIG. 16 in a compressed state with the instrument of FIG. 23 shown in cross section engaging the fastener and positioned within the plate to rotate the fastener in the direction of the arrow to compress the plate.

FIGS. 23-26 show a preferred embodiment of an instrumentation 400 used for compressing and locking plate 300. Instrumentation 400 has a working end 402 configured to cooperatively engage fastener receiving opening 330 and fastener 306. After segments 302, 304 have been attached to the adjacent vertebral bodies with an appropriate fastening element, such as bone screws, instrument 400 can be used to move segments 302, 304 toward one another to shorten the length of plate 300, create a compressive load across the disc space, and concurrently tighten fastener 306 (if desired) to secure first and second segments 302, 304 in a preferred position. Working end 402 of instrument 400 preferably has a driver portion 404 configured to cooperatively engage driver receiving opening 364 in fastener 306. Driver portion 404 is preferably hex-shaped. Working end 402 preferably has a pin 406 extending therefrom and displaced from driver portion 404 to engage one of pin receiving recesses 362a and 362b, respectively, when driver portion 404 is engaged with driver receiving opening 364 in fastener 306. With driver portion 404 engaging fastener 306 and pin 406 inserted in pin receiving recess 362b as shown in FIG. 25, instrument 400 rotates fastener 306 in the direction of arrow A as shown in FIG. 26 to move first segment 302 toward second segment 304 in the direction of arrow B to reduce the length of plate 300 and can if desired concurrently tighten fastener 306. The configuration of plate 300 provides for an internal compression mechanism that can be operated by a driver instrument eliminating the need for an externally applied compression apparatus for shortening plate 300 and creating a compressive load.

Figure 27:
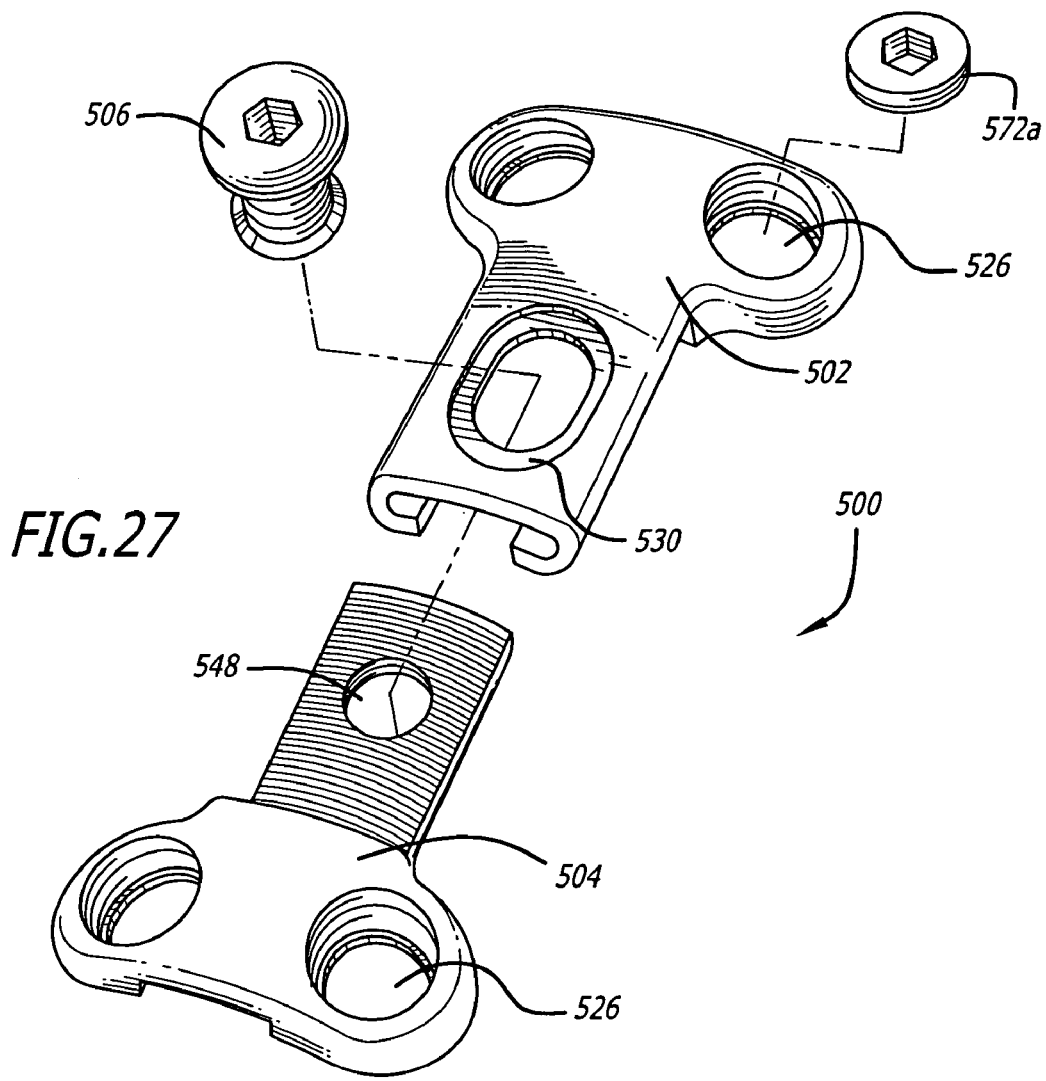
FIG. 27 is an exploded top perspective view of a plate, a fastener, and a locking element in accordance with another preferred embodiment of the present invention.
Figure 28:
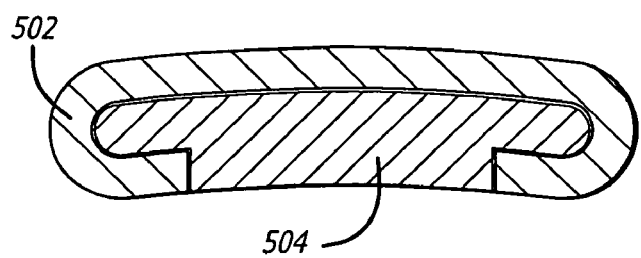
FIG. 28 is a cross sectional view transverse to the longitudinal axis of the plate of FIG. 27.
Figure 29:
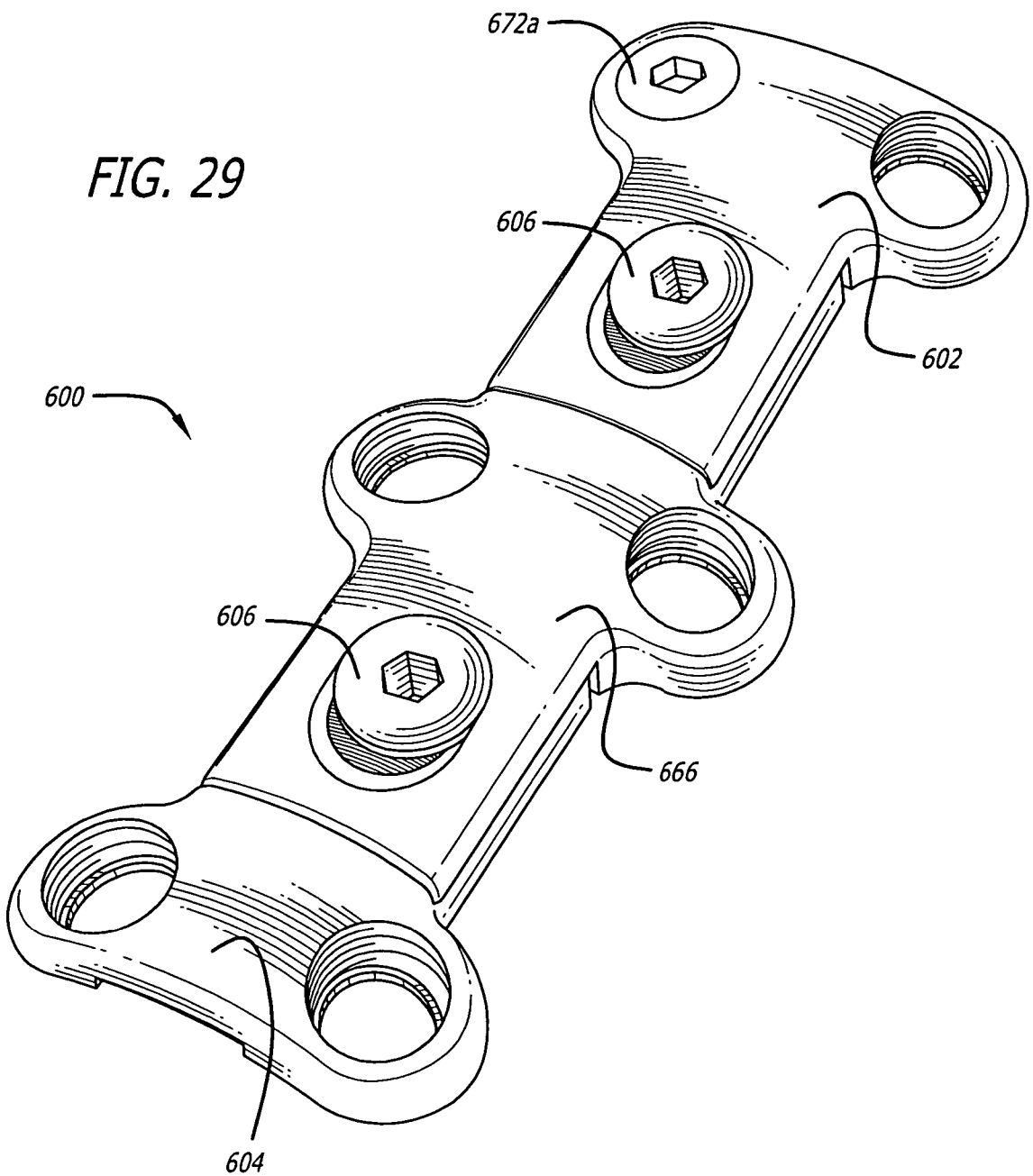
FIG. 29 is a top plan view of a plate, fasteners, and a locking element in accordance with another preferred embodiment of the present invention.
Figure 30:
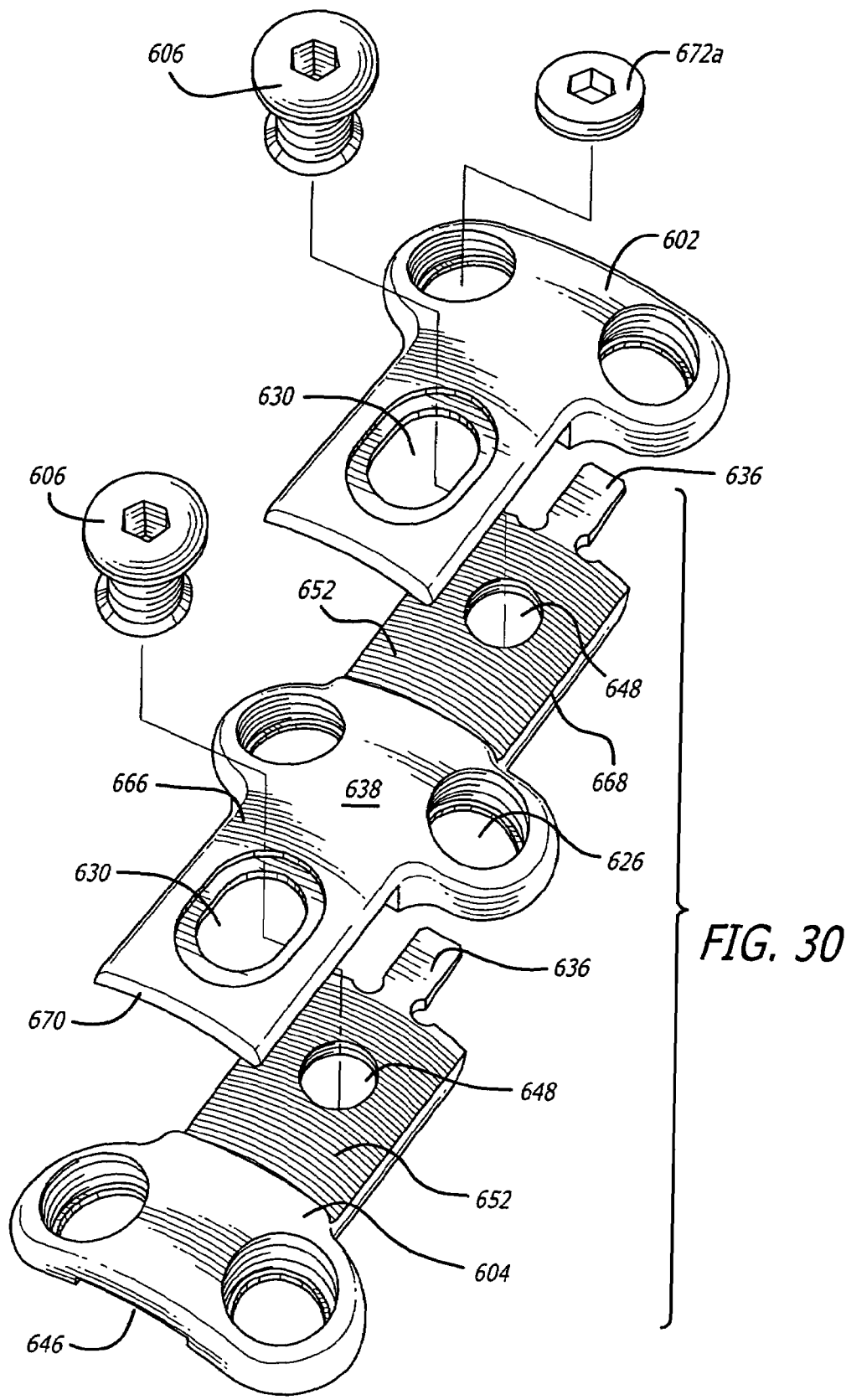
FIG. 30 is an exploded top perspective view of the plate, fasteners, and locking element of FIG. 29.
Figure 31:
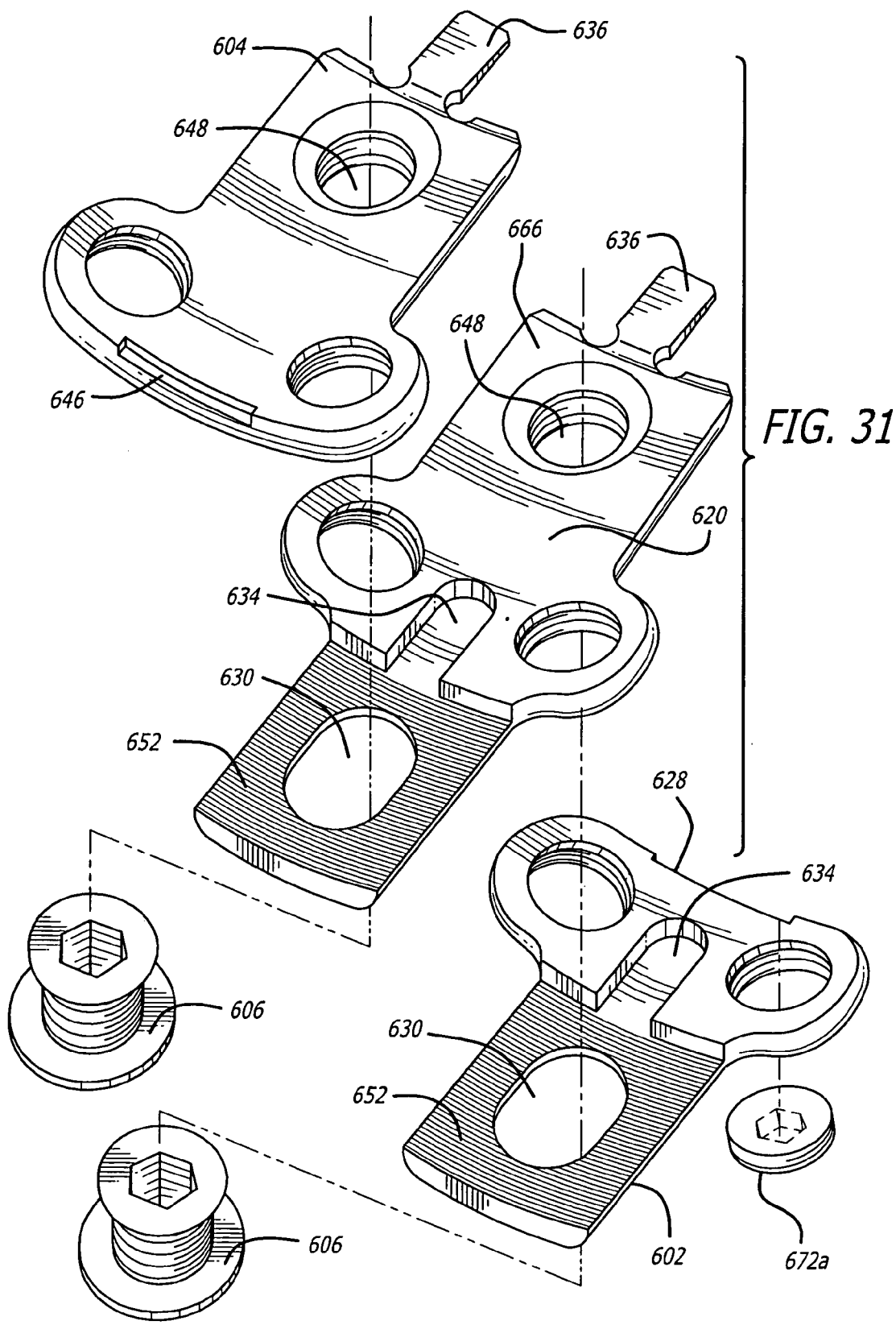
FIG. 31 is an exploded bottom perspective view of the plate, fasteners, and locking element of FIG. 29.
Figure 35:
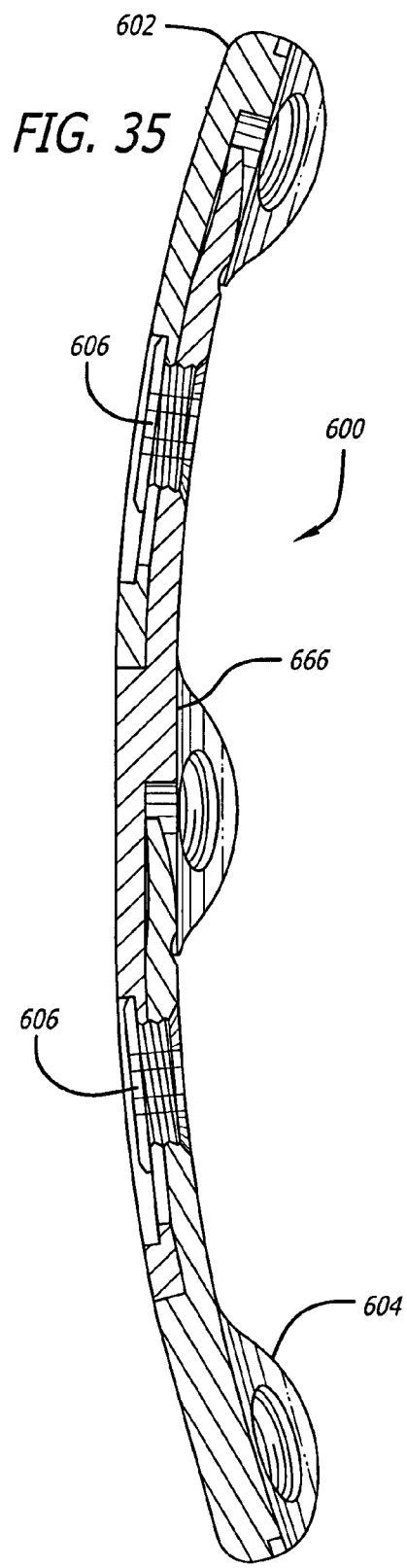
FIG. 35 is a partial cross sectional view along the longitudinal axis of the plate of FIG. 29.
Figure 36:
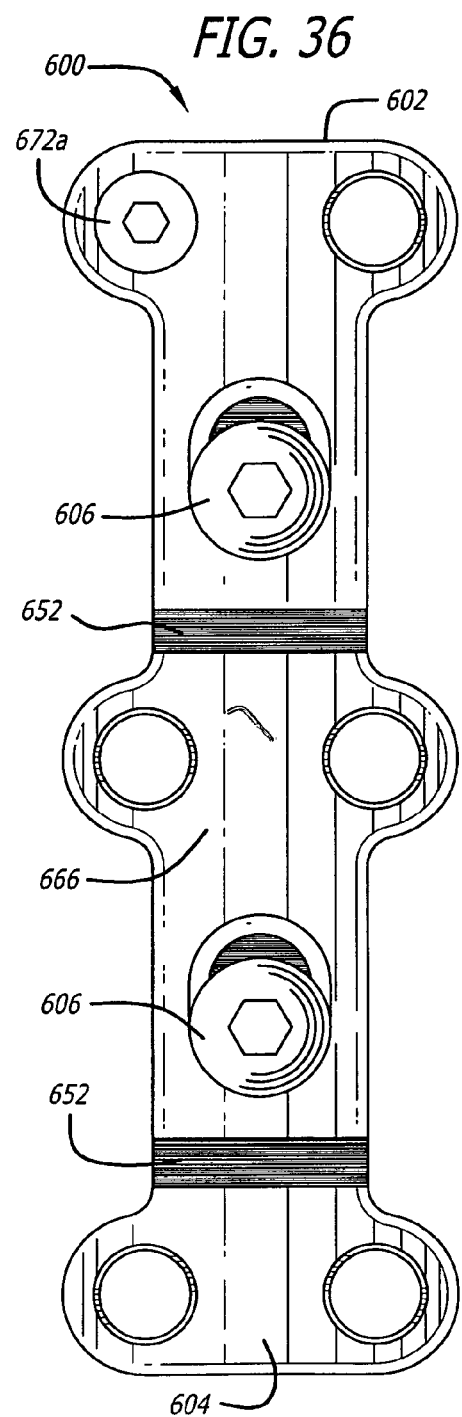
FIG. 36 is a top plan view of the plate in an elongated position, fasteners, and locking element of FIG. 29.

FIGS. 27-28 show another preferred embodiment of a cervical plate 500 in accordance with the present invention. Plate 500 is similar to plate 100 except that first segment 502 is configured to receive at least a portion of second segment 504 therein in a tongue and groove configuration. As shown in FIG. 28, first segment 502 preferably has a C-shaped cross section and second segment 504 preferably has a T-shaped cross section. The configurations of segments 502, 504 in this embodiment of the present invention keep segments 502, 504 aligned along the longitudinal axis of plate 500 and limit movement of segments 502, 504 in a direction generally transverse to the longitudinal axis of plate 500. A person of ordinary skill in the art would appreciate that other configurations of cooperatively engaging first and second segments 502, 504 are possible without departing from the intended purpose within the broad scope of the present invention.

FIGS. 29-36 show another preferred embodiment of a cervical plate 600 in accordance with the present invention. Plate 600 is similar to plate 100 except that it is configured for use across two levels of the cervical spine. In addition to the elements of plate 100, plate 600 further includes an intermediate third segment 666 between first and second segments 602, 604. Third segment 666 has a first end 668 configured to cooperatively engage first segment 602. Third segment 666 has a second end 670 configured to cooperatively engage second segment 604. Third segment 666 and first and second segments 602, 604 are articulated and can be moved to vary the spacing between the bone screw receiving holes of the plate segments as well as the overall length of the plate. Third segment 666 can be made of different lengths and/or configurations to vary the distance between first and second segments 602, 604 to further vary the spacing between the bone screw receiving holes and further vary the overall length of the plate.

First end 668 of third segment 666 has similar features to second segment 604 including a fastener receiving recess 648, bone screw receiving holes 626, ratchetings 652 on at least a portion of its upper surface 638, and a tab 636. Second end 670 of third segment 666 has similar features to first segment 602 including a ratchetings 652 on at least a portion of its lower surface 620 and a tab receiving recess 634. A first fastener 606 couples together first segment 602 to first end 668 of third segment 666. A second fastener couples together second segment 604 to second end 670 of third segment 666. Additional segments 666 may be added for use across more than two levels of the spine. Segments 666 are configured to be coupled together with first end 668 of one segment 666 to second end 670 of another segment 666.

Figure 37:
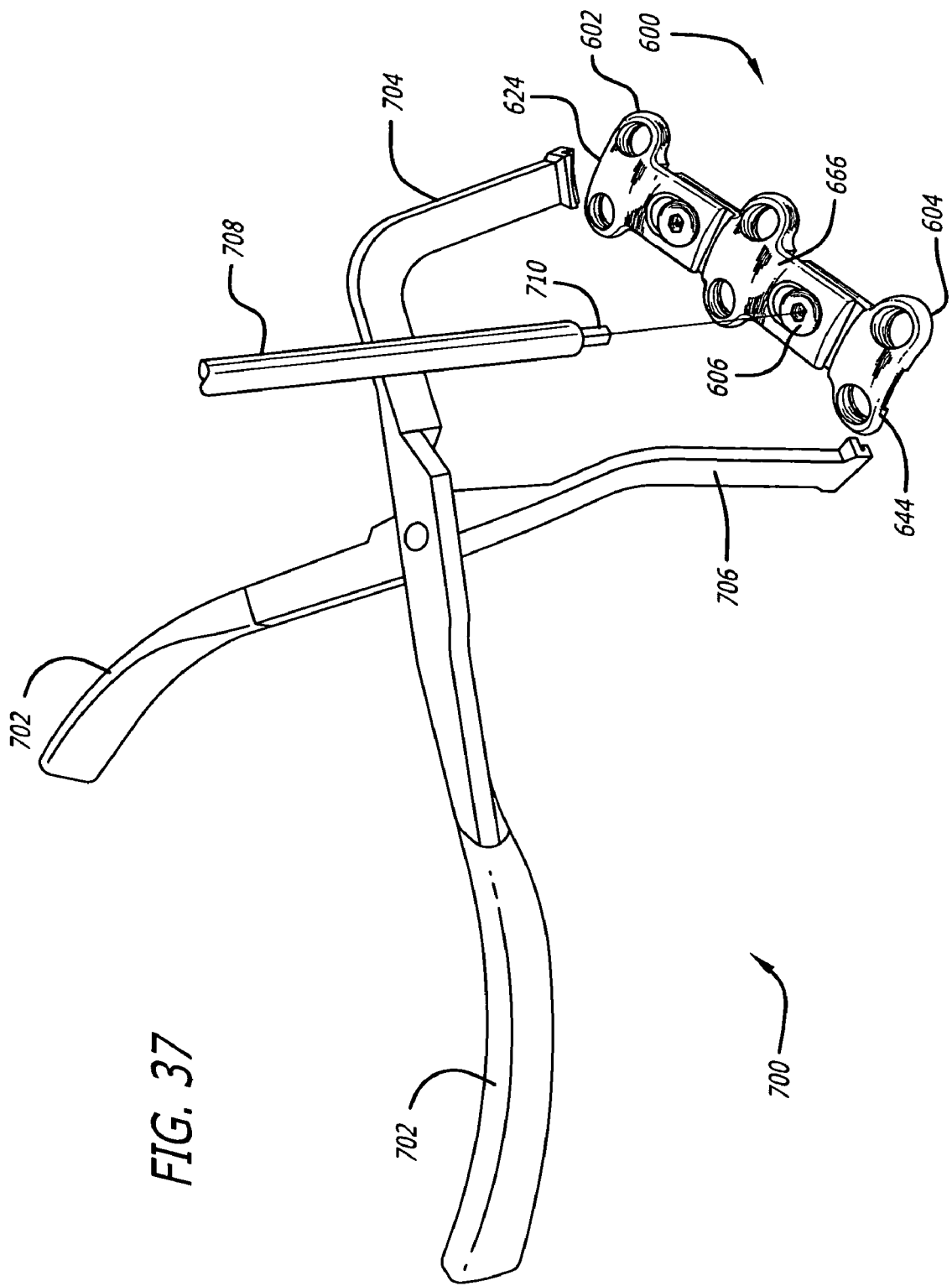
FIG. 37 is a top perspective view of the plate of FIG. 29 and another preferred embodiment of instrumentation for compressing the plate and instrumentation for locking the fastener in accordance with the present invention.

FIGS. 37-39 show a preferred embodiment of instrumentation 700 for compressing and locking plate 600. Instrumentation 700 has a handle 702 with a pair of tongs 704, 706 in moveable relationship to each. Tongs 704, 706 are configured to cooperatively engage ends 624, 644 of first and second segments, 602, 604, respectively, to shorten the overall length of the plate and to apply a desired compressive load across multiple levels of the spine. Instrumentation 700 may be used to position plate 600 in a desired position at the fusion site during at least a portion of the procedure for installing plate 600. An instrument may be used for holding the plate such as the instrumentation disclosed in the '721 patent incorporated by reference above. Instrument 700 can be used to move segments 602, 604 toward one another and toward third segment 666 to shorten the length of plate 600 and create a compressive load across the respective disc spaces.

As shown in FIG. 38, an alternative embodiment of instrument 700' may be used to move first or second segment 602, 604 toward third segment 666 so that a compressive load may be applied to one disc space at a time. Instrument 700' has a tong 704' similar to tong 704 for engaging one of ends 624, 644 of first and second segments, and forked tong 707 for engaging the third segment as shown in FIG. 38.

After the desired length of plate 600 is achieved, an instrument 708 having a head 710 configured to cooperatively engage fastener 606 is used to tighten fastener 606 to secure first, second, and third segments 602, 604, 666 in a desired position.

FIG. 40 shows another preferred embodiment of a cervical plate 800 in accordance with the present invention. Plate 800 is similar to plate 600 except that first segment 802 is configured to receive at least a portion of the first end 868 of third segment 866 therein in a tongue and groove configuration and second end 870 of third segment 866 is configured to receive at least a portion of second segment 804 therein, in a tongue and groove configuration. A person of ordinary skill in the art would appreciate that other configurations of cooperatively engaging first and second segments 802, 804 are possible without departing from the intended purpose within the broad scope of the present invention.

FIGS. 41a-41d show preferred embodiments of locking elements for locking bone screws in accordance with the present invention. For example, the bone screw locks may be in the form of a screw, a rivet, a cap, or a cover. It is appreciated that any locking element for locking a single one of the bone screws known to one of ordinary skill in the art would be within the scope of the present invention. The plate of the present invention preferably includes at least one bone screw lock adapted to lock to the plate only a single bone screw inserted into one of the bone screw receiving holes. The plate of the present invention may include more than one bone screw lock, each lock being adapted to lock to the plate only a single bone screw inserted into one of the bone screw receiving holes.

Figure 41A:
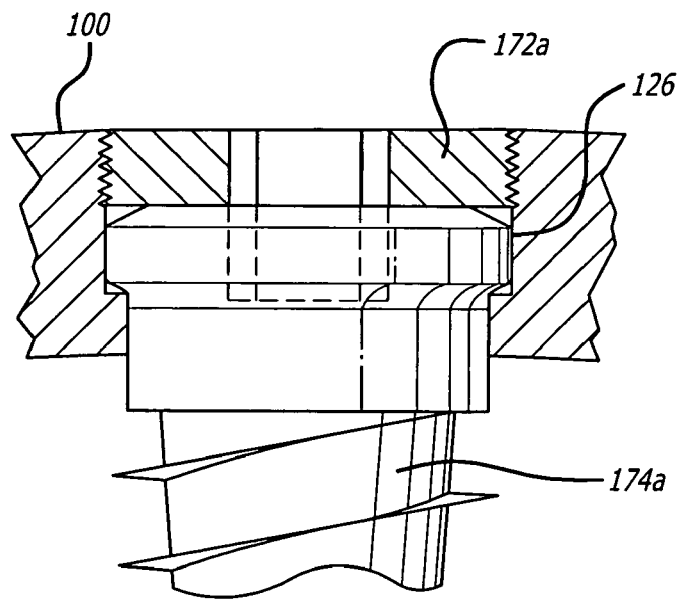
FIG. 41a is an enlarged fragmentary cross sectional view of a locking element and bone screw in accordance with a preferred embodiment of the present invention.

FIG. 41a shows an enlarged fragmentary cross sectional view of a locking element 172a and a bone screw 174a. Locking element 172a threadably engages bone screw receiving hole 126 to prevent bone screw 174a from backing out. In this embodiment, locking element 172a locks bone screw 174a in a fixed relationship to plate 100.

Figure 41B:
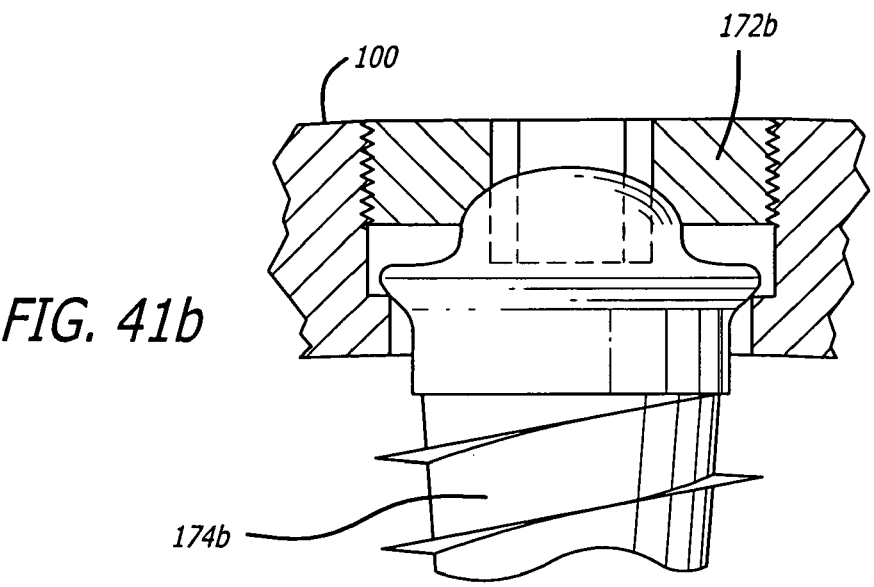
FIG. 41b is an enlarged fragmentary cross sectional view of a locking element and bone screw in accordance with another preferred embodiment of the present invention.

FIG. 41b is an enlarged fragmentary cross sectional view of a locking element 172b and a bone screw 174b. Locking element 172b threadably engages bone screw receiving hole 126 to prevent bone screw 174b from backing out. In this embodiment, locking element 172b is adapted to hold bone screw 174b in an angular relationship to plate 100. Examples of preferred fixed-angled single locking elements are taught by Michelson in U.S. Pat. No. 6,139,550, (the '550 patent) entitled "Skeletal Plating System," the disclosure of which is hereby incorporated by reference herein. Locking element 172b may also permit movement of bone screw 174b relative to plate 100.

Figure 41C:
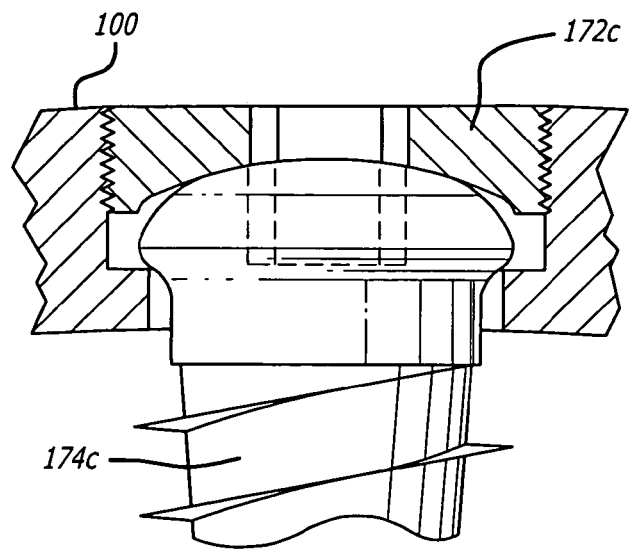
FIG. 41c is an enlarged fragmentary cross sectional view of a locking element and bone screw in accordance with yet another embodiment of the present invention.
Figure 41D:
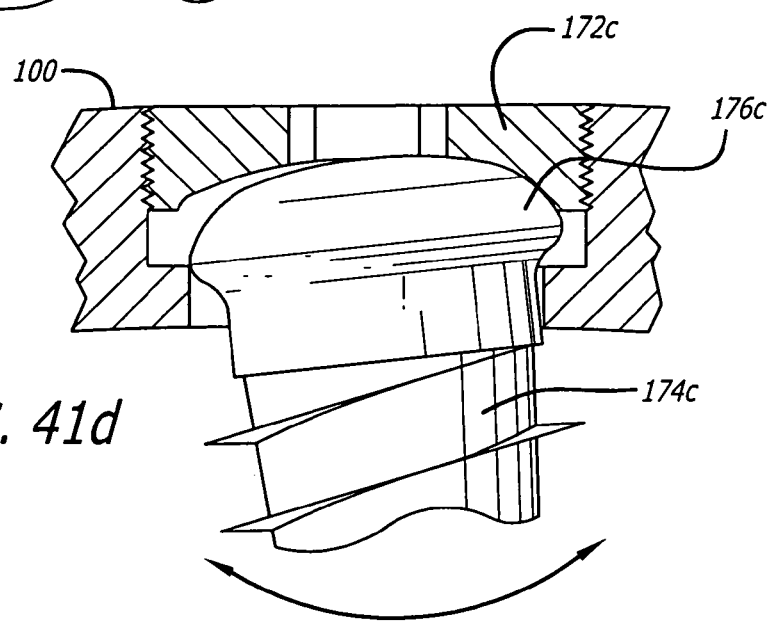
FIG. 41d is an enlarged fragmentary cross sectional view of the locking element and bone screw of FIG. 41c in an angled position.

FIGS. 41c and 41d are enlarged fragmentary cross sectional view of a locking element 172c and bone screw 174c in accordance with another embodiment of the present invention. Locking element 172c threadably engages bone screw receiving hole 126 to prevent bone screw 174c from backing out. In this embodiment, locking element 172c is adapted to hold bone screw 174c in an angular relationship to plate 100. Locking element 172c may also permit movement of bone screw 174c relative to plate 100. Locking element 172c is adapted to adjustably lock bone screw 174c in a variable angle relationship relative to plate 100. Bone screw 174c preferably has a rounded head 176c that cooperates with the bottom surface of single locking element 172c, thus allowing screw 174c to move relative to plate 100. Examples of preferred variable-angled single locking elements are taught by Michelson in the '550 patent, the disclosure of which is hereby incorporated by reference herein.

Figure 41E:
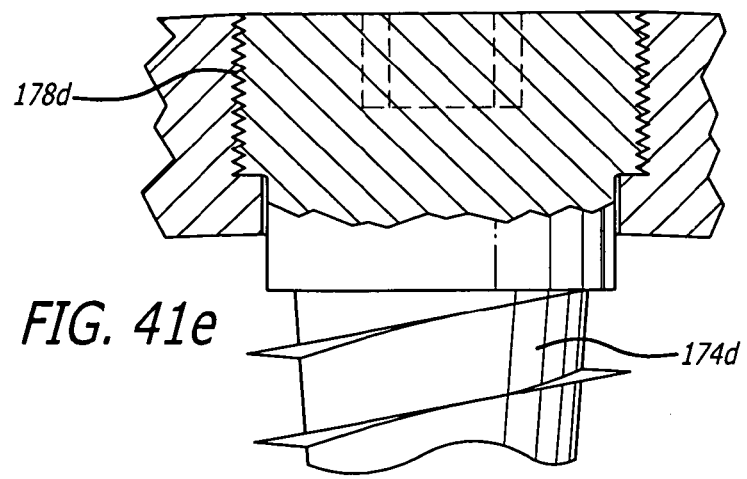
FIG. 41e is an enlarged fragmentary cross sectional view of a self-locking bone screw in accordance with a further embodiment of the present invention.

FIG. 41e is an enlarged fragmentary cross sectional view of a self-locking bone screw 174d in accordance with another embodiment of the present invention. Bone screw 174d has thread 178*d* adapted to threadably engage bone screw receiving hole 126. The thread pattern of thread 178*d* has a tighter pitch than the thread pattern of the bone engaging thread of bone screw 174*d*. The different thread pitches prevent bone screw 174*d* from backing out after installation is completed.

It is appreciated that various types of bone screws and single lock systems may be utilized with the plates of the present invention.

The plates of present invention may include a bone screw system that allows the vertebrae to move toward an interposed bone graft, and each other if necessary, instead of keeping the vertebrae apart during the occurrence of the resorption phase of the creeping substitution process. For example, the '550 patent discloses three types of screw-plate-lock systems, which are themselves combinable with one another, as follows: (1) Passive Dynamic; (2) Self-Compressing; and (3) Active Dynamic and are incorporated by reference herein. The plate of the present invention requires (1) at least one fastener non-detachably attached to the plate to prevent complete uncoupling of the plate segments from one another; and (2) at least one lock, whether separate from or part of the screw, that is adapted to lock a single bone screw only so as to prevent the screw from backing out from the bone screw receiving hole of the plate. By way of example, FIG. 41*e* shows a self-locking screw. Plates similar to that of the present invention described herein having detachable fasteners wherein the plates are adapted to be assembled and reassembled are being pursued in related applications. Plates similar to that of the present invention described herein having multilock mechanisms adapted to lock at least two bone screws as described in the '550 patent are being pursued in related applications. Various methods for using and installing the plates of the present invention are disclosed in the '550 patent and '721 patent to Michelson, incorporated by reference herein.

It is appreciated that for any of the embodiments of the plates described herein can be made of, treated, coated, combined with, comprised of, or used with any source of osteogenesis, fusion promoting substances, bone growth promoting materials, bone, bone derived substances or products, demineralized bone matrix, mineralizing proteins, ossifying proteins, bone morphogenetic proteins, hydroxyapatite, genes coding for the production of bone, substances other than bone, and bone including, but not limited to, cortical bone. The plates, screws, fasteners, and/or screw locks may also be combined with material and/or substance for inhibiting scar formation. The plates, screws, fasteners, and/or screw locks may be combined with an antimicrobial material and/or surface treated or coated to be antibacterial and/or antimicrobial, such as for example, by a silver coating. At least a portion of the bottom surface of the plates can preferably have a porous, and/or textured and/or roughened surface and may be coated with, impregnated with, or comprise of fusion promoting substances (such as bone morphogenetic proteins) so as to encourage the growth of bone along the underside of the plate from bone portion to bone portion. The textured bottom surface also provides a medium for retaining fusion promoting substances with which the bottom surface layer can be impregnated prior to installation. The bottom surface of the plate may be given the desired porous textured form by rough blasting or any other conventional technology, such as etching, plasma spraying, sintering, and casting for example. If porous so as to promote bone ingrowth, the bottom surface is formed to have a porosity or pore size in the order of 50-300 microns, and preferably 100-300 microns. Bone growth promoting substances with which the porous, textured bottom surface can be impregnated include, but are not limited to, bone morphogenetic proteins, hydroxyapatite, or hydroxyapatite tricalcium phosphate. The plate, screws, fasteners, and/or bone screw locks may include at least in part a resorbable and/or bioresorbable material which can further be impregnated with a bone growth material so that as the resorbable and/or bioresorbable material is resorbed by the body of the patient, the bone growth material is released, thus acting as a time release mechanism. The bioresorbable material may be, for example, at least in part bone. The plate of the present invention may be used in combination with a spinal fixation implant such as any object, regardless of material, that can be inserted into any portion of the spine, such as but not limited to interbody spinal implants, interbody spinal fusion implants, structural bone grafts, mesh, cages, spacers, staples, bone screws, plates, rods, tethers of synthetic cords or wires, or other spinal fixation hardware. The interbody spinal fusion implants may be at least in part bone, for example only, an allograft interbody bone graft. Alternatively, the spinal interbody spinal fusion implant may be at least in part artificial. At least one of the plate, screws, fasteners, and/or bone screw locks may be, if so desired, electrified for purposes of stimulating bone growth and contributing to bone fusion.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A plate system, comprising:
   a plate adapted to be applied to the anterior human cervical spine for contacting the anterior aspects of at least two cervical vertebral bodies to be fused, said plate comprising:
   at least a first plate segment adapted to be attached to one of the adjacent vertebral bodies to be fused and at least a second plate segment adapted to be attached to another one of the adjacent vertebral bodies to be fused, said at least first and second plate segments adapted to be connected to one another and at least in part overlapped to form said plate, said at least first and second plate segments being in a moveable relationship to one another along a longitudinal axis of said plate, each of said at least first and second plate segments including:
   a lower surface adapted to contact at least one of the cervical vertebral bodies and an upper surface opposite said lower surface, said lower surface being concave at least in part along at least a portion of the longitudinal axis of said plate;
   at least one bone screw receiving hole extending from said upper surface through said lower surface, each of said bone screw receiving holes adapted to overlie one of the cervical vertebral bodies and being adapted to receive at least one bone screw for engaging the cervical vertebral body to attach said plate to the cervical spine;
   at least one fastener adapted to couple together said first and second plate segments, said fastener being non-detachably attached to at least one of said first and second plate segments so as to prevent complete uncoupling of said first and second plate segments from one another, said fastener having a first position adapted to permit said first and second plate segments to move relative to one another along the longitudinal axis of said plate; and
   at least one bone screw lock adapted to lock to said plate only a single bone screw inserted in one of said bone screw receiving holes; and an instrument configured to cooperatively engage said fastener and at least a portion of at least one of said first and second plate segments so as upon movement of said fastener with said instrument said first and second plate segments move relative to one another along the longitudinal axis of said plate.

2. The plate system of claim 1, wherein said instrument includes a working end having at least a first portion configured to cooperatively engage said fastener and at least a second portion offset from said first portion configured to cooperatively engage at least a portion of at least one of said first and second plate segments.

3. The plate system of claim 2, wherein said instrument has a shaft terminating at said working end and having a longitudinal axis, said first portion of said working end being generally aligned with the longitudinal axis of said shaft, and said second portion of said working end being offset from the longitudinal axis of the shaft.

4. The plate system of claim 2, wherein said instrument is configured to rotate said fastener at least in part.

5. The plate system of claim 1, wherein the movement of said first and second plate segments relative to one another provides for movement of the adjacent cervical vertebral bodies toward one another.

6. The plate system of claim 1, wherein said first and second plate segments when attached to the adjacent vertebral bodies, respectively, are adapted to move toward one another in response to movement of the adjacent cervical vertebral bodies toward each other.

7. The plate system of claim 1, wherein said first and second plate segments when attached to the adjacent vertebral bodies, respectively, are adapted to move the adjacent cervical vertebral bodies toward each other.

8. The plate system of claim 1, wherein said first and second plate segments when attached to the adjacent vertebral bodies, respectively, are adapted to maintain a compressive load across a disc space between the adjacent cervical vertebral bodies when said fastener is in a second position.

9. The plate system of claim 1, wherein at least a portion of said upper surface of said second plate segment is convex at least in part along at least a portion of the longitudinal axis of said plate.

10. The plate system of claim 9, wherein said concave lower surface of said first plate segment has a radius of curvature that is different than the radius of curvature of said convex upper surface of said second plate segment.

11. The plate system of claim 1, wherein said at least first and second plate segments are configured to cooperate so as to maintain said first and second plate segments generally aligned along the longitudinal axis of said plate.

12. The plate system of claim 1, wherein said at least first and second plate segments are configured to cooperate so as to limit movement of said first and second plate segments in a direction generally transverse to the longitudinal axis of said plate.

13. The plate system of claim 1, wherein at least a portion of said lower surface of said first plate segment is configured to cooperatively engage at least a portion of said upper surface of said second plate segment.

14. The plate system of claim 1, wherein said at least a portion of said lower surface of said first plate segment is configured to interdigitate with at least a portion of said upper surface of said second plate segment.

15. The plate system of claim 14, wherein said at least a portion of said lower surface of said first plate segment and said at least a portion of the upper surface said second plate segment include ratchetings.

16. The plate system of claim 15, wherein said ratchetings are configured to permit movement of said first and second plate segments in a first direction toward one another along a mid-longitudinal axis of said plate and to restrict movement in a direction opposite to said first direction.

17. The plate system of claim 1, further comprising at least a third plate segment adapted to be connected to at least one of said first and second plate segments to form said plate.

18. The plate system of claim 17, wherein said third plate segment is an intermediate plate segment configured to be coupled between at least two plate segments.

19. The plate system of claim 1, wherein said fastener has a second position adapted to restrict movement of said first and second plate segments relative to one another along at least one direction along the longitudinal axis of said plate.

20. The plate system of claim 1, wherein said fastener passes through at least a portion of said first and second plate segments.

21. The plate system of claim 1, wherein said fastener is a rivet.

22. The plate system of claim 1, wherein said fastener is at least in part threaded.

23. The plate system of claim 1, wherein said fastener has a head.

24. The plate system of claim 23, wherein said fastener has a shaft.

25. The plate system of claim 1, wherein said at least one bone screw lock is coupled to said plate.

26. The plate system of claim 25, wherein said at least one bone screw lock is removably coupled to said plate.

27. The plate system of claim 25, wherein said at least one bone screw lock is adapted to be coupled to said plate prior to the insertion of the bone screw into said bone screw receiving hole.

28. The plate system of claim 1, wherein said at least one bone screw lock is configured to move from an initial position that permits the insertion of the bone screw into said bone screw receiving hole to a final position that is adapted to extend over at least a portion of the bone screw to retain the bone screw to said plate.

29. The plate system of claim 1, wherein said at least one bone screw lock in the final position covers at least a portion of said bone screw receiving holes.

30. The plate system of claim 1, wherein at least a portion of said at least one bone screw lock slides from the initial position to the final position.

31. The plate system of claim 30, wherein said at least one bone screw lock slides over at least a portion of one of said bone screw receiving holes.

32. The plate system of claim 31, wherein said at least one bone screw lock slides over at least a portion of the bone screws in said bone screw receiving holes.

33. The plate system of claim 1, wherein said at least one bone screw lock comprises at least one of a screw, a rivet, a cap, and a cover.

34. The plate system of claim 1, wherein said at least one bone screw lock has a central longitudinal axis and is adapted to engage a respective one of said bone screw receiving holes with the central longitudinal axis of said at least one bone screw lock being substantially coaxial with the central longitudinal axis of a respective one of said bone screw receiving holes.

35. The plate system of claim 1, wherein said at least one bone screw lock is configured to threadably engage one of said bone screw receiving holes.

36. The plate system of claim 1, wherein said at least one bone screw lock is part of a bone screw configured to threadably engage one of said bone screw receiving holes.

37. The plate system of claim 36, wherein said at least one bone screw lock has threads with different thread pitches.

38. The plate system of claim 1, wherein at least a portion of said lower surface of said first and second plate segment is concave at least in part in a direction generally transverse to the longitudinal axis of said plate.

39. The plate system of claim 38, wherein at least a portion of said lower surface of said first and second plate segments is roughened to promote the growth of bone along said lower surface.

40. The plate system of claim 1, wherein at least a portion of said lower surface of said first and second plate segments comprises a bone ingrowth surface.

41. The plate system of claim 1, wherein at least one of said bone screw receiving holes is configured to form an interference fit with at least a portion of the trailing end of a properly dimensioned bone screw to be received therein.

42. The plate system of claim 1, wherein at least one of said bone screw receiving holes is configured to hold a bone screw in fixed relationship to said plate.

43. The plate system of claim 1, wherein at least one of said bone screw receiving holes is configured to allow a bone screw to be in a moveable relationship to said plate.

44. The plate system of claim 1, wherein at least one of said bone screw receiving holes is configured to allow a bone screw to be in a variable angular relationship to said plate.

45. The plate system of claim 1, wherein at least two of said bone screw receiving holes are oriented in said plate to overlie the anterior aspect of a single cervical vertebral body adjacent a disc space to be fused.

46. The plate system of claim 1, in combination with an interbody spinal fusion implant.

47. The plate system of claim 46, wherein said implant comprises at least in part bone.

48. The plate system of claim 46, wherein said implant is an allograft interbody bone graft implant.

49. The plate system of claim 46, wherein said implant is an artificial implant.

50. The plate system of claim 1, in combination with a fusion promoting substance.

51. The plate system of claim 50, wherein said fusion promoting substance is at least in part other than bone.

52. The plate system of claim 50, wherein said fusion promoting substance is at least in part bone.

53. The plate system of claim 50, wherein said fusion promoting substance is hydroxyapatite.

54. The plate system of claim 50, wherein said fusion promoting substance comprises bone morphogenetic protein.

55. The plate system of claim 50, wherein said fusion promoting substance comprises genes coding for the production of bone.

56. The plate system of claim 1, further comprising bone screws for engaging said plate to the cervical spine, wherein at least a portion of one of said plate, said at least one bone screw lock, and said bone screws is a bioresorbable material.

57. The plate system of claim 56, wherein said bioresorbable material is at least in part bone.

58. The plate system of claim 1, in combination with a substance for inhibiting scar formation.

59. The plate system of claim 1, in combination with an antimicrobial material.

60. The plate system of claim 1, wherein said plate is treated with an antimicrobial material.

61. The plate system of claim 1, further comprising at least one bone screw having a leading end for insertion into the cervical spine and a head opposite said leading end, said at least one bone screw lock adapted to contact said head.

62. The plate system of claim 61, wherein at least one of said bone screw receiving holes has a reduced dimension proximate said lower surface of said plate to form a seat, said seat having a substantially planar surface adapted to contact a lower surface of one of said bone screws.

63. The plate system of claim 1, wherein at least one of said plate, said fastener, and said bone screw lock is electrified for purposes of stimulating bone growth and contributing to bone fusion.

* * * * *